United States Patent
Burdette et al.

(10) Patent No.: US 10,495,699 B2
(45) Date of Patent: Dec. 3, 2019

(54) METHODS AND APPARATUS FOR MAGNETIC SENSOR HAVING AN INTEGRATED COIL OR MAGNET TO DETECT A NON-FERROMAGNETIC TARGET

(71) Applicant: Allegro MicroSystems, LLC, Manchester, NH (US)

(72) Inventors: Eric Burdette, Reddick, FL (US); William P. Taylor, Amherst, NH (US)

(73) Assignee: Allegro MicroSystems, LLC, Manchester, NH (US)

( * ) Notice: Subject to any disclaimer, the term of this patent is extended or adjusted under 35 U.S.C. 154(b) by 0 days.

(21) Appl. No.: 13/946,417

(22) Filed: Jul. 19, 2013

(65) Prior Publication Data

US 2015/0022193 A1    Jan. 22, 2015

(51) Int. Cl.
*G01R 33/06* (2006.01)
*G01R 33/09* (2006.01)
*G01N 27/72* (2006.01)

(52) U.S. Cl.
CPC ............ *G01R 33/06* (2013.01); *G01N 27/72* (2013.01); *G01R 33/093* (2013.01)

(58) Field of Classification Search
CPC ...... G01D 5/147; G01D 5/145; G01D 5/2053; G01D 5/202; G01D 5/20; G01N 27/72; G01N 27/82; G01N 27/9046; G01N 27/90; G01N 27/902; G01N 27/9033; G01R 33/09; G01R 33/096; G01R 33/07; G01R 33/093; G01R 33/06; G01R 15/202; G01R 15/205; G01R 17/105; G01R 27/02; G01R 33/00; G01R 33/02; G01P 3/488; G01P 3/49; G01P 13/045; G01V 3/104; G01V 3/08; H03K 17/9505; H03K 17/954; H03K 17/952
USPC ....... 324/207.11–207.26, 228–243, 244–263, 324/164; 338/32 H, 32 R, 32 S
See application file for complete search history.

(56) References Cited

U.S. PATENT DOCUMENTS

| 3,132,337 A | * | 5/1964 | Martin | ............ H03M 1/00 310/170 |
| 3,195,043 A | | 7/1965 | Burig et al. | |
| 3,281,628 A | | 10/1966 | Bauer et al. | |
| 3,607,528 A | | 9/1971 | Gassaway | |

(Continued)

FOREIGN PATENT DOCUMENTS

| CH | 683 469 A5 | 3/1994 |
| CN | 102323554 A | 1/2012 |

(Continued)

OTHER PUBLICATIONS

U.S. Appl. No. 12/840,324, filed Jul. 21, 2010, Cesaretti et al.

(Continued)

*Primary Examiner* — Lee E Rodak
(74) *Attorney, Agent, or Firm* — Daly, Crowley, Mofford & Durkee, LLP

(57) ABSTRACT

Methods and apparatus for detecting a magnetic field include a magnetic source configured to provide a magnetic field to induce an eddy current in a non-ferromagnetic target, and a magnetic field sensing element configured to detect the magnetic field as a result of the eddy current. The magnetic field provided by the magnetic source can be a static (i.e. DC) field or a changing (i.e. non-DC) field.

16 Claims, 11 Drawing Sheets

(56) References Cited

U.S. PATENT DOCUMENTS

| | | | |
|---|---|---|---|
| 3,611,138 A * | 10/1971 | Winebrener | 324/173 |
| 3,661,061 A | 5/1972 | Tokarz | |
| 3,728,786 A | 4/1973 | Lucas et al. | |
| 4,048,670 A | 9/1977 | Eysermans | |
| 4,079,360 A | 3/1978 | Ookubo et al. | |
| 4,180,753 A * | 12/1979 | Cook, II | G01P 3/488 |
| | | | 123/146.5 A |
| 4,188,605 A | 2/1980 | Stout | |
| 4,204,317 A | 5/1980 | Winn | |
| 4,236,832 A | 12/1980 | Komatsu et al. | |
| 4,283,643 A | 8/1981 | Levin | |
| 4,315,523 A | 2/1982 | Mahawili et al. | |
| 4,438,347 A | 3/1984 | Gehring | |
| 4,490,674 A | 12/1984 | Ito | |
| 4,573,258 A | 3/1986 | Io et al. | |
| 4,614,111 A | 9/1986 | Wolff | |
| 4,649,796 A | 3/1987 | Schmidt | |
| 4,670,715 A | 6/1987 | Fuzzell | |
| 4,719,419 A | 1/1988 | Dawley | |
| 4,733,455 A | 3/1988 | Nakamura et al. | |
| 4,745,363 A | 5/1988 | Carr et al. | |
| 4,746,859 A | 5/1988 | Malik | |
| 4,752,733 A | 6/1988 | Petr et al. | |
| 4,758,943 A | 7/1988 | Aström et al. | |
| 4,760,285 A | 7/1988 | Nelson | |
| 4,764,767 A * | 8/1988 | Ichikawa et al. | 340/870.31 |
| 4,769,344 A | 9/1988 | Sakai et al. | |
| 4,772,929 A | 9/1988 | Manchester | |
| 4,789,826 A | 12/1988 | Willett | |
| 4,796,354 A | 1/1989 | Yokoyama et al. | |
| 4,823,075 A | 4/1989 | Alley | |
| 4,833,406 A | 5/1989 | Foster | |
| 4,893,027 A | 1/1990 | Kammerer et al. | |
| 4,908,685 A | 3/1990 | Shibasaki et al. | |
| 4,910,861 A | 3/1990 | Dohogne | |
| 4,935,698 A | 6/1990 | Kawaji et al. | |
| 4,944,028 A | 7/1990 | Iijima et al. | |
| 4,954,777 A * | 9/1990 | Klopfer et al. | 324/232 |
| 4,970,411 A | 11/1990 | Halg et al. | |
| 4,983,916 A | 1/1991 | Iijima et al. | |
| 4,991,447 A | 2/1991 | Yahagi et al. | |
| 5,012,322 A | 4/1991 | Guillotte | |
| 5,021,493 A | 6/1991 | Sandstrom | |
| 5,028,868 A | 7/1991 | Murata et al. | |
| 5,038,130 A | 8/1991 | Eck et al. | |
| 5,045,920 A | 9/1991 | Vig et al. | |
| 5,078,944 A | 1/1992 | Yoshino | |
| 5,084,289 A | 1/1992 | Shin et al. | |
| 5,121,289 A | 6/1992 | Gagliardi | |
| 5,137,677 A | 8/1992 | Murata | |
| 5,139,973 A | 8/1992 | Nagy et al. | |
| 5,167,896 A | 12/1992 | Hirota et al. | |
| 5,168,244 A | 12/1992 | Muranaka | |
| 5,185,919 A | 2/1993 | Hickey | |
| 5,196,794 A | 3/1993 | Murata | |
| 5,200,698 A * | 4/1993 | Thibaud | 324/207.22 |
| 5,210,493 A | 5/1993 | Schroeder et al. | |
| 5,216,405 A | 6/1993 | Schroeder et al. | |
| 5,244,834 A | 9/1993 | Suzuki et al. | |
| 5,247,202 A | 9/1993 | Popovic et al. | |
| 5,247,278 A | 9/1993 | Pant et al. | |
| 5,250,925 A | 10/1993 | Shinkle | |
| 5,289,344 A | 2/1994 | Gagnon et al. | |
| 5,286,426 A | 3/1994 | Rano, Jr. et al. | |
| 5,304,926 A | 4/1994 | Wu | |
| 5,315,245 A | 5/1994 | Schroeder et al. | |
| 5,329,416 A | 7/1994 | Ushiyama et al. | |
| 5,331,478 A | 7/1994 | Aranovsky | |
| 5,332,956 A | 7/1994 | Oh | |
| 5,332,965 A | 7/1994 | Wolf et al. | |
| 5,341,097 A | 8/1994 | Wu | |
| 5,351,028 A | 9/1994 | Krahn | |
| 5,399,968 A * | 3/1995 | Sheppard et al. | 324/242 |
| 5,412,255 A | 5/1995 | Wallrafen | |
| 5,414,355 A | 5/1995 | Davidson et al. | |
| 5,424,558 A | 6/1995 | Borden et al. | |
| 5,432,444 A | 7/1995 | Yasohama | |
| 5,434,105 A | 7/1995 | Liou | |
| 5,453,727 A | 9/1995 | Shibasaki et al. | |
| 5,469,058 A | 11/1995 | Dunnam | |
| 5,477,143 A | 12/1995 | Wu | |
| 5,479,695 A | 1/1996 | Grader et al. | |
| 5,486,759 A | 1/1996 | Seiler et al. | |
| 5,488,294 A | 1/1996 | Liddell et al. | |
| 5,491,633 A | 2/1996 | Henry et al. | |
| 5,497,081 A | 3/1996 | Wolf et al. | |
| 5,500,589 A | 3/1996 | Sumcad | |
| 5,500,994 A | 3/1996 | Itaya | |
| 5,508,611 A | 4/1996 | Schroeder et al. | |
| 5,514,953 A | 5/1996 | Schultz et al. | |
| 5,521,501 A | 5/1996 | Dettmann et al. | |
| 5,545,983 A | 8/1996 | Okeya et al. | |
| 5,551,146 A | 9/1996 | Kawabata et al. | |
| 5,552,706 A | 9/1996 | Carr | |
| 5,581,170 A | 12/1996 | Mammano et al. | |
| 5,581,179 A | 12/1996 | Engel et al. | |
| 5,583,436 A | 12/1996 | Van De Walle et al. | |
| 5,585,574 A | 12/1996 | Sugihara et al. | |
| 5,596,272 A | 1/1997 | Busch | |
| 5,621,319 A | 4/1997 | Bilotti et al. | |
| 5,627,315 A | 5/1997 | Figi et al. | |
| 5,631,557 A | 5/1997 | Davidson | |
| 5,640,090 A | 6/1997 | Furuya et al. | |
| 5,691,637 A | 11/1997 | Oswald et al. | |
| 5,696,790 A | 12/1997 | Graham et al. | |
| 5,712,562 A | 1/1998 | Berg | |
| 5,714,102 A | 2/1998 | Highum et al. | |
| 5,719,496 A | 2/1998 | Wolf | |
| 5,729,128 A | 3/1998 | Bunyer et al. | |
| 5,757,181 A | 5/1998 | Wolf et al. | |
| 5,781,005 A | 7/1998 | Vig et al. | |
| 5,789,658 A | 8/1998 | Henn et al. | |
| 5,789,915 A | 8/1998 | Ingraham | |
| 5,796,249 A | 8/1998 | Andräet et al. | |
| 5,818,222 A | 10/1998 | Ramsden | |
| 5,818,223 A | 10/1998 | Wolf | |
| 5,839,185 A | 11/1998 | Smith et al. | |
| 5,841,276 A | 11/1998 | Makino et al. | |
| 5,859,387 A | 1/1999 | Gagnon | |
| 5,886,070 A | 2/1999 | Honkura et al. | |
| 5,883,567 A | 3/1999 | Mullins, Jr. | |
| 5,912,556 A | 6/1999 | Frazee et al. | |
| 5,963,028 A | 10/1999 | Engel et al. | |
| 6,011,770 A | 1/2000 | Tan | |
| 6,016,055 A | 1/2000 | Jager et al. | |
| 6,032,536 A | 3/2000 | Peeters et al. | |
| 6,043,644 A * | 3/2000 | de Coulon | G01P 3/488 |
| | | | 324/164 |
| 6,043,646 A | 3/2000 | Jansseune | |
| 6,100,754 A | 8/2000 | Kim et al. | |
| 6,136,250 A | 10/2000 | Brown | |
| 6,169,396 B1 | 1/2001 | Yokotani et al. | |
| 6,175,232 B1 * | 1/2001 | De Coulon | G01D 5/2006 |
| | | | 324/207.12 |
| 6,175,233 B1 | 1/2001 | McCurley et al. | |
| 6,180,041 B1 | 1/2001 | Takizawa | |
| 6,184,679 B1 | 2/2001 | Popovic et al. | |
| 6,194,893 B1 | 2/2001 | Yokotani et al. | |
| 6,198,373 B1 | 3/2001 | Ogawa et al. | |
| 6,242,604 B1 | 6/2001 | Hudlicky et al. | |
| 6,242,904 B1 | 6/2001 | Shirai et al. | |
| 6,242,905 B1 | 6/2001 | Draxelmayr | |
| 6,265,865 B1 | 7/2001 | Engel et al. | |
| 6,278,269 B1 | 8/2001 | Vig et al. | |
| 6,291,989 B1 | 9/2001 | Schroeder | |
| 6,297,627 B1 | 10/2001 | Towne et al. | |
| 6,297,628 B1 | 10/2001 | Bicking et al. | |
| 6,323,642 B1 | 11/2001 | Nishimura et al. | |
| 6,339,322 B1 | 1/2002 | Loreck et al. | |
| 6,351,506 B1 | 2/2002 | Lewicki | |
| 6,356,068 B1 | 3/2002 | Steiner et al. | |
| 6,366,079 B1 | 4/2002 | Uenoyama | |
| 6,392,478 B1 | 5/2002 | Mulder et al. | |
| 6,429,640 B1 | 8/2002 | Daughton et al. | |

(56) References Cited

U.S. PATENT DOCUMENTS

| | | | |
|---|---|---|---|
| 6,436,748 B1 | 8/2002 | Forbes et al. |
| 6,437,558 B2 | 8/2002 | Li et al. |
| 6,452,381 B1 | 9/2002 | Nakatani et al. |
| 6,462,536 B1* | 10/2002 | Mednikov et al. ...... 324/207.16 |
| 6,492,804 B2 | 12/2002 | Tsuge et al. |
| 6,501,270 B1 | 12/2002 | Opie |
| 6,504,363 B1 | 1/2003 | Dogaru et al. |
| 6,525,531 B2 | 2/2003 | Forrest et al. |
| 6,528,992 B2 | 3/2003 | Shinjo et al. |
| 6,542,847 B1 | 4/2003 | Lohberg et al. |
| 6,545,332 B2 | 4/2003 | Huang |
| 6,545,457 B2 | 4/2003 | Goto et al. |
| 6,545,462 B2 | 4/2003 | Schott et al. |
| 6,566,862 B1* | 5/2003 | Goto ................... G01D 3/0365 |
| | | | 324/207.16 |
| 6,566,872 B1 | 5/2003 | Sugitani |
| 6,590,804 B1 | 7/2003 | Perner |
| 6,640,451 B1* | 11/2003 | Vinarcik ....................... 33/1 PT |
| 6,653,968 B1 | 11/2003 | Schneider |
| 6,674,679 B1 | 1/2004 | Perner et al. |
| 6,687,644 B1 | 2/2004 | Zinke et al. |
| 6,692,676 B1 | 2/2004 | Vig et al. |
| 6,759,843 B2 | 7/2004 | Furlong |
| 6,770,163 B1 | 8/2004 | Koah et al. |
| 6,781,233 B2 | 8/2004 | Zverev et al. |
| 6,781,359 B2 | 8/2004 | Stauth et al. |
| 6,798,193 B2 | 9/2004 | Zimmerman et al. |
| 6,815,944 B2 | 11/2004 | Vig et al. |
| 6,822,443 B1 | 11/2004 | Dogaru |
| 6,853,178 B2 | 2/2005 | Hayat-Dawoodi |
| 6,896,407 B2 | 5/2005 | Nomiyama et al. |
| 6,902,951 B2 | 6/2005 | Goller et al. |
| 6,917,321 B1 | 7/2005 | Haurie et al. |
| 7,019,516 B2 | 3/2006 | Tokunaga et al. |
| 7,023,205 B1 | 4/2006 | Krupp |
| 7,026,808 B2 | 4/2006 | Vig et al. |
| 7,031,170 B2 | 4/2006 | Daeche et al. |
| 7,038,448 B2 | 5/2006 | Schott et al. |
| 7,049,924 B2* | 5/2006 | Hayashi ............... G01D 5/2046 |
| | | | 324/207.17 |
| 7,112,955 B2 | 9/2006 | Buchhold |
| 7,112,957 B2 | 9/2006 | Bicking |
| 7,126,327 B1* | 10/2006 | Busch ...................... 324/207.21 |
| 7,132,825 B2 | 11/2006 | Martin |
| 7,184,876 B2 | 2/2007 | Teulings et al. |
| 7,190,784 B2 | 3/2007 | Li |
| 7,193,412 B2 | 3/2007 | Freeman |
| 7,199,579 B2 | 4/2007 | Scheller et al. |
| 7,259,545 B2 | 8/2007 | Stauth et al. |
| 7,265,531 B2 | 9/2007 | Stauth et al. |
| 7,269,992 B2 | 9/2007 | Lamb et al. |
| 7,285,952 B1 | 10/2007 | Hatanaka et al. |
| 7,292,095 B2 | 11/2007 | Burt et al. |
| 7,295,000 B2 | 11/2007 | Werth |
| 7,319,319 B2 | 1/2008 | Jones et al. |
| 7,323,780 B2 | 1/2008 | Daubenspeck et al. |
| 7,323,870 B2 | 1/2008 | Tatschl et al. |
| 7,325,175 B2 | 1/2008 | Momtaz |
| 7,345,468 B2 | 3/2008 | Okada et al. |
| 7,355,388 B2 | 4/2008 | Ishio |
| 7,361,531 B2 | 4/2008 | Sharma et al. |
| 7,362,094 B2 | 4/2008 | Voisine et al. |
| 7,365,530 B2 | 4/2008 | Bailey et al. |
| 7,385,394 B2 | 6/2008 | Auburger et al. |
| 7,425,821 B2 | 9/2008 | Monreal et al. |
| 7,474,093 B2 | 1/2009 | Ausserlechner |
| 7,476,953 B2 | 1/2009 | Taylor et al. |
| 7,518,354 B2 | 4/2009 | Stauth et al. |
| 7,592,801 B2 | 9/2009 | Bailey et al. |
| 7,598,601 B2 | 10/2009 | Taylor et al. |
| 7,605,647 B1 | 10/2009 | Romero et al. |
| 7,635,993 B2 | 12/2009 | Boeve |
| 7,694,200 B2 | 4/2010 | Forrest et al. |
| 7,701,208 B2 | 4/2010 | Nishikawa |
| 7,705,586 B2 | 4/2010 | Van Zon et al. |
| 7,729,675 B2 | 6/2010 | Krone |
| 7,746,056 B2 | 6/2010 | Stauth et al. |
| 7,746,065 B2 | 6/2010 | Pastre et al. |
| 7,764,118 B2 | 7/2010 | Kusuda et al. |
| 7,768,083 B2 | 8/2010 | Doogue et al. |
| 7,769,110 B2 | 8/2010 | Momtaz |
| 7,800,389 B2 | 9/2010 | Friedrich et al. |
| 7,808,074 B2 | 10/2010 | Knittl |
| 7,816,772 B2 | 10/2010 | Engel et al. |
| 7,816,905 B2 | 10/2010 | Doogue et al. |
| 7,839,141 B2 | 11/2010 | Werth et al. |
| 7,923,996 B2 | 4/2011 | Doogue et al. |
| 7,936,144 B2 | 5/2011 | Vig et al. |
| 7,956,604 B2 | 6/2011 | Ausserlechner |
| 7,961,823 B2 | 6/2011 | Kolze et al. |
| 7,990,209 B2 | 8/2011 | Romero |
| 8,030,918 B2 | 10/2011 | Doogue et al. |
| 8,058,870 B2 | 11/2011 | Sterling |
| 8,063,631 B2 | 11/2011 | Fermon et al. |
| 8,063,634 B2 | 11/2011 | Sauber et al. |
| 8,080,993 B2 | 12/2011 | Theuss et al. |
| 8,089,276 B2 | 1/2012 | Kentsch |
| 8,106,649 B2* | 1/2012 | Kaita .................... G01D 5/145 |
| | | | 324/207.25 |
| 8,106,654 B2 | 1/2012 | Theuss et al. |
| 8,128,549 B2 | 3/2012 | Testani et al. |
| 8,134,358 B2 | 3/2012 | Charlier et al. |
| 8,143,169 B2 | 3/2012 | Engel et al. |
| 8,253,210 B2 | 8/2012 | Theuss et al. |
| 8,274,279 B2* | 9/2012 | Gies .............................. 324/240 |
| 8,362,579 B2 | 1/2013 | Theuss et al. |
| 8,559,139 B2 | 10/2013 | Theuss |
| 8,610,430 B2 | 12/2013 | Werth et al. |
| 8,624,588 B2 | 1/2014 | Vig et al. |
| 8,773,124 B2 | 7/2014 | Ausserlechner |
| 9,116,018 B2 | 8/2015 | Frachon |
| 9,164,156 B2 | 10/2015 | Elian et al. |
| 9,201,123 B2 | 12/2015 | Elian et al. |
| 2001/0002791 A1 | 6/2001 | Tsuge et al. |
| 2001/0009367 A1 | 7/2001 | Seitzer et al. |
| 2001/0026153 A1* | 10/2001 | Nakamura ............ G01D 5/145 |
| | | | 324/207.2 |
| 2002/0027488 A1 | 3/2002 | Hayat-Dawoodi et al. |
| 2002/0084923 A1 | 7/2002 | Li |
| 2002/0097639 A1 | 7/2002 | Ishizaki et al. |
| 2003/0001563 A1 | 1/2003 | Turner |
| 2003/0038675 A1 | 2/2003 | Gailus et al. |
| 2003/0062891 A1* | 4/2003 | Slates .................... G01B 7/001 |
| | | | 324/207.26 |
| 2003/0102909 A1 | 6/2003 | Motz |
| 2003/0107366 A1 | 6/2003 | Busch et al. |
| 2003/0151406 A1 | 8/2003 | Wan et al. |
| 2003/0173955 A1 | 9/2003 | Uenoyama |
| 2003/0222642 A1 | 12/2003 | Butzmann |
| 2003/0227286 A1* | 12/2003 | Dunisch ............... G01P 15/003 |
| | | | 324/207.16 |
| 2004/0032251 A1 | 2/2004 | Zimmerman et al. |
| 2004/0046248 A1 | 3/2004 | Waelti et al. |
| 2004/0062362 A1 | 4/2004 | Matsuya |
| 2004/0080314 A1 | 4/2004 | Tsujii et al. |
| 2004/0135220 A1 | 7/2004 | Goto |
| 2004/0155647 A1 | 8/2004 | Stauth et al. |
| 2004/0174164 A1 | 9/2004 | Ao |
| 2004/0184196 A1 | 9/2004 | Jayasekara |
| 2004/0189285 A1 | 9/2004 | Uenoyama |
| 2004/0196045 A1* | 10/2004 | Larsen .................... G01V 3/104 |
| | | | 324/329 |
| 2004/0252563 A1 | 12/2004 | Hokuto et al. |
| 2004/0263014 A1* | 12/2004 | Miya ....................... G01D 3/10 |
| | | | 310/168 |
| 2005/0017709 A1* | 1/2005 | Stolfus ................... F01D 17/06 |
| | | | 324/174 |
| 2005/0120782 A1 | 6/2005 | Kishibata et al. |
| 2005/0122095 A1* | 6/2005 | Dooley ................... F01D 17/06 |
| | | | 324/174 |
| 2005/0122099 A1* | 6/2005 | Imamoto ............ G01N 27/9046 |
| | | | 324/239 |
| 2005/0167790 A1 | 8/2005 | Khor et al. |

(56) References Cited

U.S. PATENT DOCUMENTS

| | | |
|---|---|---|
| 2005/0179429 A1 | 8/2005 | Lohberg |
| 2005/0225318 A1 | 10/2005 | Bailey et al. |
| 2005/0280411 A1 | 12/2005 | Bicking |
| 2006/0033487 A1 | 2/2006 | Nagano et al. |
| 2006/0038559 A1* | 2/2006 | Lamb et al. ............... 324/242 |
| 2006/0038561 A1 | 2/2006 | Honkura et al. |
| 2006/0068237 A1 | 3/2006 | Murphy |
| 2006/0097717 A1* | 5/2006 | Tokuhara ............... G01D 3/022 324/207.25 |
| 2006/0125473 A1 | 6/2006 | Frachon et al. |
| 2006/0175674 A1 | 8/2006 | Taylor |
| 2006/0181263 A1 | 8/2006 | Doogue et al. |
| 2006/0202692 A1 | 9/2006 | Tatschl et al. |
| 2006/0238190 A1 | 10/2006 | Ishio |
| 2006/0261801 A1 | 11/2006 | Busch |
| 2007/0110199 A1 | 5/2007 | Momtaz et al. |
| 2007/0170533 A1 | 7/2007 | Doogue et al. |
| 2007/0247141 A1 | 10/2007 | Pastre et al. |
| 2007/0285089 A1 | 12/2007 | Ibuki et al. |
| 2008/0012558 A1 | 1/2008 | Rossler et al. |
| 2008/0013298 A1 | 1/2008 | Sharma et al. |
| 2008/0094055 A1 | 4/2008 | Monreal et al. |
| 2008/0116884 A1 | 5/2008 | Rettig et al. |
| 2008/0116885 A1 | 5/2008 | Van Zon et al. |
| 2008/0137784 A1 | 6/2008 | Krone |
| 2008/0211492 A1 | 9/2008 | Tsukada et al. |
| 2008/0237818 A1 | 10/2008 | Engel et al. |
| 2008/0238410 A1 | 10/2008 | Charlier et al. |
| 2009/0001964 A1 | 1/2009 | Strzalkowski |
| 2009/0001972 A1 | 1/2009 | Fernandez et al. |
| 2009/0009163 A1 | 1/2009 | Yamada |
| 2009/0058404 A1 | 3/2009 | Kurumado |
| 2009/0085706 A1 | 4/2009 | Baarman et al. |
| 2009/0102467 A1* | 4/2009 | Snell et al. ............... 324/207.25 |
| 2009/0137398 A1 | 5/2009 | Bozovic et al. |
| 2009/0140725 A1 | 6/2009 | Ausserlechner |
| 2009/0146647 A1 | 6/2009 | Ausserlechner |
| 2009/0152696 A1 | 6/2009 | Dimasacat et al. |
| 2009/0167298 A1* | 7/2009 | Kreutzbruck et al. ........ 324/235 |
| 2009/0167301 A1 | 7/2009 | Ausserlechner |
| 2009/0168266 A1 | 7/2009 | Berkley et al. |
| 2009/0189600 A1 | 7/2009 | Kurkovskiy |
| 2009/0206827 A1 | 8/2009 | Aimuta et al. |
| 2009/0206831 A1* | 8/2009 | Fermon et al. ............... 324/240 |
| 2009/0212765 A1 | 8/2009 | Doogue et al. |
| 2009/0243601 A1* | 10/2009 | Feldtkeller ......... H03K 17/9505 324/207.26 |
| 2009/0251134 A1 | 10/2009 | Uenoyama |
| 2009/0256552 A1 | 10/2009 | Guo et al. |
| 2009/0315543 A1 | 12/2009 | Guo et al. |
| 2010/0026279 A1 | 2/2010 | Vig et al. |
| 2010/0026288 A1 | 2/2010 | Sauber |
| 2010/0033175 A1 | 2/2010 | Boeve et al. |
| 2010/0045268 A1 | 2/2010 | Kilian |
| 2010/0052667 A1 | 3/2010 | Kohama et al. |
| 2010/0053789 A1 | 3/2010 | Duric et al. |
| 2010/0072988 A1 | 3/2010 | Hammerschmidt et al. |
| 2010/0141249 A1 | 6/2010 | Ararao et al. |
| 2010/0188078 A1 | 7/2010 | Foletto et al. |
| 2010/0201356 A1 | 8/2010 | Koller et al. |
| 2010/0207620 A1 | 8/2010 | Gies |
| 2010/0211347 A1 | 8/2010 | Friedrich et al. |
| 2010/0237450 A1 | 9/2010 | Doogue et al. |
| 2010/0276769 A1 | 11/2010 | Theuss et al. |
| 2010/0295140 A1 | 11/2010 | Theuss et al. |
| 2010/0330708 A1 | 12/2010 | Engel et al. |
| 2011/0004278 A1 | 1/2011 | Aghassian et al. |
| 2011/0018533 A1 | 1/2011 | Cesaretti et al. |
| 2011/0031960 A1 | 2/2011 | Hohe et al. |
| 2011/0048102 A1 | 3/2011 | Fernandez et al. |
| 2011/0074405 A1 | 3/2011 | Doogue et al. |
| 2011/0127998 A1 | 6/2011 | Elian et al. |
| 2011/0187354 A1 | 8/2011 | Zieren et al. |
| 2011/0224537 A1 | 9/2011 | Brunner |
| 2011/0267040 A1 | 11/2011 | Frachon |
| 2011/0285384 A1 | 11/2011 | Nomura |
| 2011/0298448 A1 | 12/2011 | Foletto et al. |
| 2012/0007589 A1 | 1/2012 | Okada |
| 2012/0013333 A1 | 1/2012 | Ararao et al. |
| 2012/0019236 A1 | 1/2012 | Tiernan et al. |
| 2012/0019239 A1 | 1/2012 | Decitre |
| 2012/0062215 A1 | 3/2012 | Ide et al. |
| 2012/0086090 A1 | 4/2012 | Sharma et al. |
| 2012/0249133 A1 | 10/2012 | Friedrich |
| 2012/0274314 A1 | 11/2012 | Cesaretti et al. |
| 2012/0293167 A1* | 11/2012 | Kitanaka ............... G01D 5/147 324/207.25 |
| 2012/0303305 A1* | 11/2012 | Bergqvist ............... G01D 5/225 702/65 |
| 2013/0015845 A1 | 1/2013 | Fox |
| 2013/0113474 A1 | 5/2013 | Elian |
| 2013/0147470 A1 | 6/2013 | Mulholland et al. |
| 2013/0207648 A1 | 8/2013 | Zibold et al. |
| 2013/0214774 A1 | 8/2013 | Cesaretti et al. |
| 2013/0214777 A1 | 8/2013 | Itoi |
| 2013/0241543 A1 | 9/2013 | Stenson et al. |
| 2013/0278246 A1 | 10/2013 | Stegerer et al. |
| 2013/0300401 A1 | 11/2013 | Krapf et al. |
| 2013/0300406 A1 | 11/2013 | Pepka et al. |
| 2014/0084906 A1 | 3/2014 | Ruigrok et al. |
| 2014/0175584 A1 | 6/2014 | Foletto et al. |
| 2014/0176126 A1 | 6/2014 | Friedrich et al. |
| 2014/0184214 A1 | 7/2014 | Schäffer et al. |
| 2014/0232379 A1 | 8/2014 | Nazarian et al. |
| 2014/0266176 A1 | 9/2014 | Fernandez et al. |
| 2014/0327435 A1 | 11/2014 | Rohrer |
| 2014/0333295 A1 | 11/2014 | Fernandez et al. |
| 2015/0022193 A1 | 1/2015 | Burdette et al. |
| 2015/0022198 A1 | 1/2015 | David et al. |
| 2015/0211895 A1 | 7/2015 | Reitsma et al. |
| 2015/0236869 A1 | 8/2015 | Vreeland et al. |
| 2015/0323612 A1 | 11/2015 | Latham |
| 2016/0069662 A1 | 3/2016 | Mullenix et al. |
| 2016/0123774 A1 | 5/2016 | Foletto et al. |

FOREIGN PATENT DOCUMENTS

| | | |
|---|---|---|
| CN | 102483443 A | 5/2012 |
| CN | 102713654 A | 10/2012 |
| CN | 102954808 A | 3/2013 |
| DE | 25 18 054 | 11/1976 |
| DE | 40 31 560 | 4/1992 |
| DE | 195 39 458 A1 | 4/1997 |
| DE | 68927973 T2 | 9/1997 |
| DE | 196 34 715 A1 | 3/1998 |
| DE | 196 50 935 A1 | 6/1998 |
| DE | 198 38 433 | 3/1999 |
| DE | 19851839 A1 | 11/1999 |
| DE | 199 61 504 A1 | 6/2001 |
| DE | 102 10 184 | 9/2003 |
| DE | 103 14 602 A1 | 10/2004 |
| DE | 10 2006 037 226 A1 | 2/2008 |
| DE | 10 2007 018 238 A1 | 10/2008 |
| DE | 10 2007 041 230 B3 | 4/2009 |
| DE | 10 2010 016 584 | 11/2010 |
| DE | 10 2010 016 584 A1 | 11/2010 |
| DE | 10 2011 102483 | 11/2012 |
| EP | 0 289 414 A2 | 11/1988 |
| EP | 0 289 414 A3 | 11/1988 |
| EP | 0 357 013 A2 | 3/1990 |
| EP | 0 357 013 A3 | 3/1990 |
| EP | 0 361 456 A2 | 4/1990 |
| EP | 0 361 456 A3 | 4/1990 |
| EP | 0 504 583 | 9/1992 |
| EP | 0629834 A1 | 12/1994 |
| EP | 0 680 103 A1 | 11/1995 |
| EP | 0 898 180 A2 | 2/1999 |
| EP | 0 944 888 B1 | 10/2001 |
| EP | 1306687 A2 | 5/2003 |
| EP | 1 443 332 A1 | 8/2004 |
| EP | 1 580 560 A1 | 9/2005 |
| EP | 1 637 898 A1 | 3/2006 |
| EP | 1 662 353 A1 | 5/2006 |
| EP | 1 679 524 A1 | 7/2006 |

(56) References Cited

FOREIGN PATENT DOCUMENTS

| | | | |
|---|---|---|---|
| EP | 1 850 143 A1 | 10/2007 | |
| EP | 2 063 229 | 5/2009 | |
| EP | 2 063 229 A1 | 5/2009 | |
| EP | 1797496 | 7/2009 | |
| EP | 2402719 A1 | 1/2012 | |
| EP | 2402719 A1 | 1/2012 | |
| EP | 2 685 273 A1 | 1/2014 | |
| EP | 2 730 893 A1 | 5/2014 | |
| FR | 2 748 105 | 10/1997 | |
| FR | 2 909 756 | 6/2008 | |
| GB | 2135060 A * | 8/1984 | ............ E21B 47/10 |
| GB | 2276727 A | 10/1994 | |
| GB | 2481482 | 12/2011 | |
| JP | 60-152950 | 8/1985 | |
| JP | 61-48777 | 3/1986 | |
| JP | S6367583 A | 3/1988 | |
| JP | 363 084176 A | 4/1988 | |
| JP | 63-263782 | 10/1988 | |
| JP | 63-300911 | 12/1988 | |
| JP | H02-116753 | 5/1990 | |
| JP | 02-149013 | 6/1990 | |
| JP | H03-29817 | 2/1991 | |
| JP | H04-095817 | 3/1992 | |
| JP | 04-152688 | 5/1992 | |
| JP | H06-273437 | 9/1994 | |
| JP | 08-97486 | 4/1996 | |
| JP | H08-511348 A | 11/1996 | |
| JP | 09-166612 | 6/1997 | |
| JP | 10-38988 | 2/1998 | |
| JP | H1038988 | 2/1998 | |
| JP | 10-332725 | 12/1998 | |
| JP | H10318784 | 12/1998 | |
| JP | 11-064363 | 3/1999 | |
| JP | 11-74142 | 3/1999 | |
| JP | 2000-183241 A | 6/2000 | |
| JP | 2001-043475 | 2/2001 | |
| JP | 2001-141738 A | 5/2001 | |
| JP | 2001-153683 A | 6/2001 | |
| JP | 2001-165702 | 6/2001 | |
| JP | 2001-1659951 | 6/2001 | |
| JP | 2002-117500 | 4/2002 | |
| JP | 2002-149013 | 5/2002 | |
| JP | 2002-357920 | 12/2002 | |
| JP | 2003-177171 | 6/2003 | |
| JP | 2003-202365 A | 7/2003 | |
| JP | 2003-287439 A | 10/2003 | |
| JP | 2004-055932 | 2/2004 | |
| JP | 2004-093381 | 3/2004 | |
| JP | 2004-152688 | 5/2004 | |
| JP | 2004-356338 | 12/2004 | |
| JP | 2004-357858 | 12/2004 | |
| JP | 2005-517928 | 6/2005 | |
| JP | 2005-337866 | 12/2005 | |
| JP | 2005-345302 | 12/2005 | |
| JP | 2006-003096 | 1/2006 | |
| JP | 2006-3116 A | 1/2006 | |
| JP | 2006-003116 A | 1/2006 | |
| JP | 2006-275764 | 10/2006 | |
| JP | 2007-012582 A | 1/2007 | |
| JP | 2007-218799 | 8/2007 | |
| JP | 2007-240202 | 9/2007 | |
| JP | 2008-180550 | 8/2008 | |
| JP | 2008-264569 | 11/2008 | |
| JP | 2008-286667 A | 11/2008 | |
| JP | 2009-002911 A | 1/2009 | |
| JP | 2009-222524 | 10/2009 | |
| JP | 2009-250725 A | 10/2009 | |
| JP | 2009-250931 A | 10/2009 | |
| JP | 2010-537207 A | 12/2010 | |
| JP | 2012-501446 A | 1/2012 | |
| KR | 2012-0040247 A | 4/2012 | |
| KR | 2013 0019872 A | 2/2013 | |
| WO | WO 88/09026 | 11/1988 | |
| WO | WO 93/12403 | 6/1993 | |
| WO | WO 1993/12403 | 6/1993 | |
| WO | WO 94/08203 | 4/1994 | |
| WO | WO 1994/08203 | 4/1994 | |
| WO | WO 94/29672 A1 | 12/1994 | |
| WO | WO 95/18982 | 7/1995 | |
| WO | WO 1995/18982 | 7/1995 | |
| WO | WO 96/02849 A1 | 2/1996 | |
| WO | WO 1999/49322 | 9/1999 | |
| WO | WO 2001/74139 A2 | 10/2001 | |
| WO | WO 2001/74139 A3 | 10/2001 | |
| WO | WO 2003/069358 A2 | 8/2003 | |
| WO | WO 2003/069358 A3 | 8/2003 | |
| WO | WO 2003/107018 A1 | 12/2003 | |
| WO | WO 2004/027436 | 4/2004 | |
| WO | WO 2004/072672 A1 | 8/2004 | |
| WO | WO 2005/013363 A2 | 2/2005 | |
| WO | WO 2005/013363 A3 | 2/2005 | |
| WO | WO 2006/035342 | 4/2006 | |
| WO | WO 2006/056829 | 6/2006 | |
| WO | WO 2006/083479 | 8/2006 | |
| WO | WO2007/095971 A1 | 8/2007 | |
| WO | WO 2007/138508 A1 | 12/2007 | |
| WO | WO 2008/008140 A2 | 1/2008 | |
| WO | WO 2008/008140 A3 | 1/2008 | |
| WO | WO 2008/048379 A1 | 4/2008 | |
| WO | WO 2008/121443 A1 | 10/2008 | |
| WO | WO 2008/145662 A1 | 12/2008 | |
| WO | WO 2009/108422 A2 | 9/2009 | |
| WO | WO 2009/108422 A3 | 9/2009 | |
| WO | WO 2010/014309 A1 | 2/2010 | |
| WO | WO 2010/027658 A2 | 3/2010 | |
| WO | WO 2010/065315 | 6/2010 | |
| WO | WO 2010/096367 A1 | 8/2010 | |
| WO | WO 2011/011479 | 1/2011 | |
| WO | WO 2012/148646 | 11/2012 | |
| WO | WO 2013/169455 | 11/2013 | |
| WO | WO2015/058733 A1 | 4/2015 | |

OTHER PUBLICATIONS

U.S. Appl. No. 12/959,672, filed Dec. 3, 2010, Doogue et al.
U.S. Appl. No. 12/968,353, filed Dec. 15, 2010, Donovan et al.
U.S. Appl. No. 13/095,371, filed Apr. 27, 2011, Cesaretti et al.
U.S. Appl. No. 13/350,970, filed Jan. 16, 2012, Milano et al.
U.S. Appl. No. 13/398,127, filed Feb. 16, 2012, Cesaeretti et al.
U.S. Appl. No. 13/424,618, filed Mar. 20, 2012, Doogue et al.
U.S. Appl. No. 13/526,106, filed Jun. 18, 2012, Vig et al.
Ahn et al., "A New Toroidal-Meander Type Integrated Inductor With a Multilevel Meander Magnetic Core", IEEE Transactions on Magnetics, vol. 30, No. 1, Jan. 1994, pp. 73-79.
Allegro "Two-Wire True Zero Speed Minature Differential Peak-Detecting Gear Tooth Sensor;" ATS645LSH; 2004; Allegro MircoSystems, Inc., Worcester, MA 01615; pp. 1-14.
Allegro Microsystems, Inc. Data Sheet A1341; "High Precision, Highly Programmable Linear Hall Effect Sensor IC with EEPROM, Output Potocols SENT and PWM, and Advanced Output Linearization Capabilities;" May 17, 2010; 46 pages.
Allegro Microsystems, Inc. Data Sheet ATS601LSG; "Non-TPOS, Tooth Detecting Speed Sensor;" Nov. 1, 2011; 9 pages.
Allegro Microsystems, Inc., "Gear-Tooth Sensor For Automotive Applications," Aug. 3, 2001.
Allegro Microsystems, Inc. Hall-Effect IC Applications Guide, http://www.allegromicro.com/en/Products/Design/an/an27701.pdf, Copyright 1987, 1997, pp. 1-36.
Allegro "True Zero-Speed Low-Jitter High Accuracy Gear Tooth Sensor;" ATS625LSG; 2005; Allegro MicroSystems, Inc. Worcester, MA 01615; pp. 1-21.
Ausserlechner et al.; "Compensation of the Piezo-Hall Effect in Integrated Hall Sensors on (100)-Si;" IEEE Sensors Journal, vol. 7, No. 11; Nov. 2007; ISBN: 1530-437X; pp. 1475-1482.
Ausserlechner et al.; "Drift of Magnetic Sensitivity of Small Hall Sensors Due to Moisture Absorbed by the IC-Package;" Proceedings of IEEE Sensors, 2004; vol. 1; Oct. 24, 2004; ISBN:0-7803-8692-2; pp. 455-458.
Ausserlechner; "Limits of Offset Cancellation by the Principle of Spinning Current Hall Probe;" Proceedings of IEEE Sensors; Oct. 2004; pp. 1117-1120.

(56) References Cited

OTHER PUBLICATIONS

Ausserlechner; "The piezo-Hall effect in n-silicon for arbitrary crystal orientation;" Proceedings of IEEE Sensors; vol. 3; Oct. 24, 2004; ISBN: 0-7803-8692-2; pp. 1149-1152.
Bahreyni, et al.; "A Resonant Micromachined Magnetic Field Sensor;" IEEE Sensors Journal; vol. 7, No. 9, Sep. 2007; pp. 1326-1334.
Barrettino, et al.; "CMOS-Based Monolithic Controllers for Smart Sensors Comprising Micromembranes and Microcantilevers;" IEEE Transactions on Circuits and Systems—I Regular Papers vol. 54, No. 1; Jan. 2007; pp. 141-152.
Baschirotto et al.; "Development and Analysis of PCB Vector 2-D Magnetic Field Sensor System for Electronic Compass;" IEEE Sensors Journal vol. 6, No. 2; Apr. 2006; pp. 365-371.
Bilotti et al.; "Monolithic Magnetic Hall Sensor Using Dynamic Quadrature Offset Cancellation:" IEEE Journal of Solid-State Circuits; vol. 32, Issue 6; Jun. 1997: pp. 829-836.
Bowers et al., "Microfabrication and Process Integration of Powder-Based Permanent Magnets", Interdisciplinary Microsystems Group, Dept. Electrical and Computer Engineering, University of Florida, USA; Technologies for Future Micro-Nano Manufacturing Workshop, Napa, California, Aug. 8-10, 2011, pp. 162-165.
Demierre, et al.; "Reference Magnetic Actuator for Self-Calibration of a Very Small Hall Sensor Array;" Sensors and Actuators A97-98; Apr. 2002; pp. 39-46.
Dwyer, "Back-Biased Packaging Advances (SE, SG & SH versus SA & SB)" http://www.allegromicro.com/en/Products/Design/packaging_advances/index.asp, Copyright 2008, pp. 1-5.
Frick, et al.; "CMOS Microsystem for AC Current Measurement with Galvanic isolation;" IEEE Sensors Journal; vol. 3, No. 6; Dec. 2003; pp. 752-760.
Halg; "Piezo-Hall Coefficients of n-Type Silicon;" Journal of Applied Physics; vol. 64, No. 1; Jul. 1, 1988; pp. 276-282.
Honeywell International, Inc., "Hall Effect Sensing and Application," Micro Switch Sensing and Control, Chapter 3, http://content.honeywell.com/sensing/prodinfo/solidstate/technical/hallbook.pdf. date unavailable but believed to be before Jan. 2008, pp. 9-18.
Hosticka; "CMOS Sensor Systems;" Sensors and Actuators A66; Apr. 1998; pp. 335-341.
Infineon Product Brief, TLE 4941plusC, Differential Hall IC for Wheel Speed Sensing, Oct. 2010, www.infineon.com/sensors, 2 pages.
Infineon Technologies; "Differential Two-Wire Hall Effect Sensor IC;" TLE4942 Preliminary Data Sheet; Jun. 2000; pp. 1-13.
Johnson et al., "Hybrid Hall Effect Device," Appl. Phys. Lett., vol. 71, No. 7, Aug. 1997, pp. 974-976.
Kanda at al.; "The Piezo-Hall Effect in n-Silicon;" $22^{nd}$ International Conference on the Physics of Semiconductors; vol. 1, Jan. 1995; pp. 89-92.
Krammerer et al.: "A Hall effect sensors network insensitive to mechanical stress;" Proceedings of IEEE Sensors; vol. 3, Oct. 2004; pp. 1071-1074.
Lagorce et al.; "Magnetic and Mechanical Properties of Micromachined Strontium Ferrite/Polyimide Composites:" Journal of Microelectromechanical Systems; vol. 6, No. 4; Dec. 1997; pp. 307-312.
Lequesne et al.; "High-Accuracy Magnetic Position Encoder Concept;" IEEE Transactions on Industry Applications; vol. 35, No. 3; May/Jun. 1999; pp. 568-576.
Magnani et al.; "Mechanical Stress Mesurement Electronics Based on Piezo-Resistive and Piezo-Hall Effects;" $9^{th}$ International Conference on Electronics, Circuits and Systems 2002; vol. 1; SBN:0-7803-7596-3; Dec. 2002; pp. 363-366.
Manic et al.; "Short and Long-Term Stability Problems of Hall Plates in Plastic Packages:" IEEE $38^{th}$ Annual International Reliability Physics Symposium; Apr. 2000; pp. 225-230.
Manic; "Drift in Silicon Integrated Sensors and Circuits Due to the Thermo-Mechanical Stresses;" Lausanne École Polytechnique Feédérale De Lausanne 2000; Part 1 of 2; 74 pages.

Manic; "Drift in Silicon Integrated Sensors and Circuits Due to the Thermo-Mechanical Stresses;" Lausanne, École Polytechnique Feédérale De Lausanne 2000; Part 2 of 2; 102 pages.
Melexis Microelectronic Systems, Hall Applications Guide, Section 3—Applications, 1997 (48 pages).
Motz et al.; "An Integrated Magnetic Sensor with Two Continuous-Time $\Delta\Sigma$-Converters and Stress Compensation Capability;" IEEE International Solid-State Circuits Conference; Digest of Technical Papers; Feb. 6, 2006; ISBN: 1-4244-0079-1; pp. 1151-1160.
Motz, et al.; "A Chopped Hall Sensor with Small Jitter and Programmable "True Power-On" Function;" IEEE Journal of Solid-State Circuits; vol. 40, No. 7; Jul. 2005; pp. 1533-1540.
Motz, et al.; "An integrated Hall Sensor Platform Design for Position, Angle and Current Sensing;" IEEE Sensors 2006; Exco, Daegu, Korea / Oct. 22-25, 2006; pp. 1008-1011.
Munter; "A Low-offset Spinning-current Hall Plate:" Sensors and Actuators A21-A23; 1990; pp. 742-746.
Munter; "Electronic Circuitry for a Smart Spinning-current Hall Plate with Low Offset:" Sensors and Actuators A; Jun. 1991;.pp. 747-751.
Oniku et al., "High-Energy-Density Permanent Micromagnets Formed From Heterogeneous Magnetic Powder Mixtures", Interdisciplinary Microsystems Group, Dept. of Electrical and Computer Engineering, University of Florida, Gainesville, FL 32611, USA; Preprint of MEMS 2012 Conf. Paper, 4 pages.
Park et al.: "Batch-Fabricated Microinductors with Electroplated Magnetically Anisotropic and Laminated Alloy Cores", IEEE Transactions on Magnetics, vol. 35, No. 5, Sep. 1999, 10 pages.
Park et al.; "Ferrite-Based Integrated Planar Inductors and Transformers Fabricated at Low Temperature;" IEEE Transactions on Magnetics; vol. 33, No. 5; Sep. 1997; pp. 3322-3324.
Partin et al.; "Temperature Stable Hall Effect Sensors;" IEEE Sensors Journal, vol. 6, No. 1; Feb. 2006; pp. 106-110.
Pastre, et al.; "A Hall Sensor Analog Front End for Current Measurement with Continuous Gain Calibration;" IEEE Sensors Journal; vol. 7, No. 5; May 2007; pp. 860-867.
Pastre, et al.; "A Hall Sensor-Based Current Measurement Miorosystem With Continuous Gain Calibration;" Research in Microelectronics and Electronics, IEEE vol. 2; Jul. 25, 2005; ISBN: 0-7803-9345-7; pp. 95-98.
Popovic; "Sensor Microsystems;" Proc. $20^{th}$ International Conference on Microelectronics (MWIL 95); vol. 2, NIS, Serbia, 12-14; Sep. 1995; pp. 531-537.
Randhawa; "Monolithic Integrated Hall Devices in Silicon Circuits;" Microelectronics Journal; vol. 12, No. 6; Sep. 14-17, 1981; pp. 24-29.
Robert Bosch GMBH Stuttgart; "Active Sensor for ABS/ASR/VDC-Systems with 2-Wire-Current Interface;" Specification TLE4941/TLE4942; Version 5; Jun. 25, 2000; 44 pages.
Ruther et al.; "Integrated CMOS-Based Sensor Array for Mechanical Stress Mapping;" $5^{th}$ IEEE Conference on Sensors, Oct. 2007; pp. 1131-1134.
Ruther et al.; "Thermomagnetic Residual Offset in Integrated Hall Plates;" IEEE Sensors Journal; vol. 3, No. 6; Dec. 2003; pp. 693-699.
Sargent; "Switched-capacitor IC controls feedback loop:" EDN; Design ideas; Feb. 17, 2000; pp. 154 and 156.
Schneider; "Temperature Calibration of CMOS Magnetic Vector Probe for Contactless Angle Measurement System," IEDM 1996 pp. 533-536.
Schott et al.; "Linearizing Integrated Hall Devices;" 1997 International Conference on Sold-State Sensors and Actuators, Jun. 16-19, 1997; pp. 393-396.
Schott, et al.; "CMOS Single-Chip Eiectronic Compass with Microcontroller;" IEEE Journal of Sold-State Circuits; vol. 42, No. 12; Dec. 2007; pp. 2923-2933.
Simon et al.; "Autocalibration of Silicon Hall Devices:" $8^{th}$ International Conference on Sold-State Sensors and Actuators; vol. 2; Jun. 25, 1995; pp. 237-240.
Smith et al.; "Low Magnetic Field Sensing with GMR Sensors;" Sensor Magazine; Part 1; Sep. 1999; http://archives.sensorsmag.com/articles/0999/76mail.shtml; pp. 1-8.

(56) References Cited

OTHER PUBLICATIONS

Smith et al.; "Low Magnetic Field Sensing with GMR Sensors;" Sensor Magazine; Part 2; Oct. 1999; http://archives.sensorsmag.com/articles/1099/84/mail.shtml; pp. 1-11.
Steiner et al.; "Doubie-Hall Sensor with Self-Compensated Offset;" International Electron Devices Meeting; Dec. 7, 1997; ISBN: 0-7803-4100-7; pp. 911-914.
Steiner et al; Offset Reduction in Hall Devices by Continuous Spinning Current Method; Sensors and Actuators A66; 1998; pp. 167-172.
Stellrecht et al.; Characterization of Hygroscopic Swelling Behavior of Mold Compounds and Plastic Packages; IEEE Transactions on Components and Packaging Technologies; vol. 27, No. 3; Sep. 2004; pp. 499-506.
Tian et al.; "Multipie Sensors on Pulsed Eddy-Current Detection for 3-D Subsurface Crack Assessment;" IEEE Sensors Journal, vol. 5, No. 1; Feb. 2005; pp. 90-96.
Trontelj et al: "CMOS Integrated Magnetic Field Source Used as a Reference in Magnetic Field Sensors on Common Substrate;" WEP 1-6; IMTC; May 1994; pp. 461-463.
Wu, et al.; "A Chopper Current-Feedback Instrumentation Amplifier with a 1mHz 1/f Noise Corner and an AC-Coupled Ripple-Reduction Loop;" IEEE International Solid-State Circuits Conference; Feb. 10, 2009; pp. 322-324.
Zou et al.; "Three-Dimensional Die Surface Stress Measurements in Delaminated and Non-Delaminated Plastic Packages;" 48th Electronic Components and Technology Conference; May 25, 1998; pp. 1223-1234.
Office Action/Restriction Requirement dated May 14, 2010; for U.S. Appl. No. 12/037,393; 6 pages.
Response to Office Action/Restriction Requirement dated May 14, 2010; for U.S. Appl. No. 12/037,393; 6 pages.
Office Action dated Jun. 30, 2010; for U.S. Appl. No. 12/037,393; 21 pages.
Response to Office Action dated Jun. 30, 2010; for U.S. Appl. No. 12/037,393; 34 pages.
Notice of Allowance dated Nov. 3, 2010; for U.S. Appl. No. 12/037,393; 7 pages.
Request for Continued Examination dated Jan. 25, 2011; for U.S. Appl. No. 12/037,393; 1 page.
Notice of Allowance dated Feb. 11, 2011; for U.S. Appl. No. 12/037,393; 8 pages.
Office Action dated Feb. 2, 2011; for U.S. Appl. No. 12/959,672; 13 pages.
Response to Office Action dated Feb. 2, 2011; for U.S. Appl. No. 12/959,672; 8 pages.
Notice of Allowance dated Jun. 27, 2011; for U.S. Appl. No. 12/959,672; 8 pages.
Request for Continued Examination dated Jul. 12, 2011; for U.S. Appl. No. 12/959,672; 2 pages.
Notice of Allowance dated Jul. 19, 2011; for U.S. Appl. No. 12/959,672; 8 pages.
Office Action/Restriction Requirement dated Apr. 12, 2012; for U.S. Appl. No. 12/183,367; 6 pages.
Response to Office Action/Restriction Requirement dated Apr. 12, 2013; for U.S. Appl. No. 12/183,367;2 pages.
Office Action dated May 2, 2011; for U.S. Appl. No. 12/183,367; 17 pages.
Response to Action dated May 12, 2011; for U.S. Appl. No. 12/183,367; 13 pages.
Office Acton dated Oct. 20, 2011; for U.S. Appl. No. 12/183,367; 11 pages.
Supplemental Response to Restriction Requirement dated Feb. 6, 2013; for U.S. Appl. No. 12/183,367; 2 pages.
Response to Office Action dated Oct. 20, 2011; for U.S. Appl. No. 12/183,367; 15 pages.
Fiinal Office Action dated May 2, 2013; for U.S. Appl. No. 12/183,367; 15 pages.
Response to Final Office Action dated May 2, 2013; for U.S. Appl. No. 12/183,367; 8 pages.
Final Office Action dated Jul. 1, 2013; for U.S. Appl. No. 12/183,367; 6 pages.
Final Office Action dated Jul. 23, 2013; for U.S. Appl. No. 12/183,367; 8 pages.
Response to Office Action dated Jul. 23, 2013; for U.S. Appl. No. 12/183,367; 13 pages.
Notice of Allowance dated Sep. 6, 2013; for U.S. Appl. No. 12/183,367; 7 pages.
Office Action dated Jun. 7, 2012; for U.S. Appl. No. 12/360,889; 9 pages.
Response to Office Action dated Jun. 7, 2012; for U.S. Appl. No. 12/360,889; 11 pages.
Office Action dated Jan. 18, 2013; for U.S. Appl. No. 12/360,889; 7 pages.
Response to Office Action dated Jan. 18, 2013; for U.S. Appl. No. 12/360,889; 6 pages.
Office Action dated Jun. 28, 2013; for U.S. Appl. No. 12/360,889; 7 pages.
Responose to Office Action dated Jun. 28, 2013; for U.S. Appl. No. 12/360,889; 15 pages.
Office Action/Restriction Requirement dated Oct. 23, 2009; for U.S. Appl. No. 12/328,798; 7 pages.
Response to Office Action/Restriction Requiremenet dated Oct. 23, 2009; for U.S. Appl. No. 12/328,798; 1 page.
Office Action dated Dec. 14, 2009; for U.S. Appl. No. 12/328,798; 20 pages.
Response to Office Action dated Dec. 14, 2009; for U.S. Appl. No. 12/328,798; 22 pages.
Office Action dated May 24, 2010; for U.S. Appl. No. 12/328,798; 22 pages.
Response to Office Action dated May 24, 2010; for U.S. Appl. No. 12/328,798; 23 pages.
Office Action dated Oct. 31, 2011; for U.S. Appl. No. 12/328,798; 23 pages.
Response to Office Action dated Oct. 31, 2011; for U.S. Appl. No. 12/328,798; 14 pages.
Final Office Action dated May 10, 2012; for U.S. Appl. No. 12/328,798; 17 pages.
Response to Final Office Action dated May 10, 2012; for U.S. Appl. No. 12/328,798; 6 pages.
Request for Continued Examination dated Aug. 9, 2012; for U.S. Appl. No. 12/328,798; 1 page.
Notice of Allowance dated Oct. 26, 2012; for U.S. Appl. No. 12/328,798; 13 pages.
Request for Continued Examination dated Jan. 24, 2013; for U.S. Appl. No. 12/328,798; 3 pages.
Notice of Allowance dated Mar. 1, 2013; for U.S. Appl. No. 12/328,798; 10 pages.
Office Action dated Feb. 22, 2012; for U.S. Appl. No. 13/241,380; 23 pages.
Response to Office Action dated Feb. 22, 2012; for U.S. Appl. No. 13/241,380; 16 pages.
Office Action dated Jul. 19, 2012; for U.S. Appl. No. 13/241,380; 18 pages.
Response to Office Action dated Jul. 19, 2012; for U.S. Appl. No. 13/241,380; 6 pages.
Notice of Allowance dated Oct. 29, 2012; for U.S. Appl. No. 13/241,380; 23 pages.
Request for Continued Examination dated Jan. 24, 2013; for U.S. Appl. No. 13/241,380; 3 pages.
Notice of Allowance dated Feb. 21, 2013; for U.S. Appl. No. 13/241,380; 9 pages.
Office Action dated Jul. 6, 2012; for U.S. Appl. No. 12/706,318; 29 pages.
Response to Office Action dated Jul. 6, 2012; for U.S. Appl. No. 12/706,318; 12 pages.
Supplemental Response to Office Action dated Jul. 6, 2012; for U.S. Appl. No. 12/706,318; 12 pages.
Notice of Allowance dated Dec. 10, 2012; for U.S. Appl. No. 12/706,318; 9 pages.
Office Action dated Sep. 11, 2012; for U.S. Appl. No. 12/840,324; 30 pages.

(56) References Cited

OTHER PUBLICATIONS

Response to Office Action dated Sep. 11, 2012; for U.S. Appl. No. 12/840,324; 15 pages.
Final Office Action dated Feb. 12, 2013; for U.S. Appl. No. 12/840,324; 19 pages.
Response to Final Office Action dated Feb. 12, 2013; for U.S. Appl. No. 12/840,324; 12 pages.
Notice of Allowance dated May 24, 2013; for U.S. Appl. No. 12/840,324; 12 pages.
Corrected Notice of Allowability dated Jul. 17, 2013; for U.S. Appl. No. 12/840,324; 7 pages.
Corrected Notice of Allowability dated Aug. 9, 2013; for U.S. Appl. No. 12/840,324; 6 pages.
Office Action dated Jun. 11, 2013; for U.S. Appl. No. 13/095,371; 31 pages.
Response to Office Action dated Jun. 11, 2013; for U.S. Appl. No. 13/095,371; 25 pages.
Notice of Allowance dated Oct. 28, 2013; for U.S. Appl. No. 13/095,371; 19 pages.
European Board of Appeals Decision dated Feb. 28, 2005; for European Pat. App. No. 03 710 766.1; 14 pages.
European Communication for the Board of Appeals dated Apr. 30, 2009; for European Pat. App. No. 03 710 766.1; 2 pages.
European Board of Appeals Datasheet for the Decision dated Nov. 22, 2007; for European Pat. App. No. 03 710 766.1; 22 pages.
European Preliminary Amendment from the Board of Appeal dated May 26, 2009; for European Pat. App. No. 03 710 766.1; pages.
Letter from Yuasa and Hara dated Jun. 4, 2008; Japanese First Office Action dated Apr. 7, 2008; for JP Pat. App. No. 2009-568426; 5 pages.
Letter from Yuasa and Hara dated Oct. 21, 2008; Japanese Response to First Office Action filed Sep. 22, 2008; for JP Pat. App. No. 2009-568426; 14 pages.
Letter from Yuasa and Hara dated Dec. 12, 2008; Japanese Second Office Action; for JP Pat. App. No. 2009-568426; 4 pages.
Letter from Yuasa and Hara dated Apr. 23, 2009; Japanese Response to Second Office Action filed Mar. 25, 2009; for JP Pat. App. No. 2009-568426; 8 pages.
Letter from Yuasa and Hara dated Jan. 17, 2011; Japanese Third Office Action dated Feb. 16, 2011; for JP Pat. App. No. 2009-568426; 5 pages.
Letter from Yuasa and Hara dated Jun. 9, 2011; Japanese Response to Third Office Acton filed May 13, 2011; for JP Pat. App. No. 2009-568426; 27 pages.
Japanese Notice of Allowance dated Nov. 8, 2011; for Japanese Pat. App. No. 2009-568426; 3 pages.
Letter from NTD Patent & Trademark Agency Limited dated Oct. 13, 2010; for Chinese Pat. App. No. 200880008895.3; 2 pages.
Chinese Office Action (with English translation) dated Sep. 9, 2010; for Chinese Pat. App. No. 200880008895.3; 12 pages.
Letter from NTD Patent & Trademark Agency Limited dated Mar. 28, 2011; for Chinese Pat. App. No. 200880008895.3; 1 page.
Chinese Response to Office Action dated Mar. 28, 2011; for Chinese Pat. App. No. 200880008895.3; 7 pages.
Chinese Notice of Allowance (with English translation) dated Jul. 4, 2011; for Chinese Pat. App. No. 200880008895.3; 4 pages.
Letter from Yuasa and Hara dated Jul. 26, 2012; for Japanese Pat. App. No. 2010-201028; 5 pages.
Japanese First Office Action (English translation) dated Jul. 26, 2012; for Japanese Pat. App. No. 2010-201028; 5 pages.
Letter from Yuasa and Hara dated Oct. 16, 2012; for Japanese Pat. App. No. 2010-201028; 2 pages.
Japanese Response to First Office Action (with English translation) dated Oct. 16, 2012; for Japanese Pat. App. No. 2010-201028; 10 pages.
Letter from Yuasa and Hara dated Aug. 7, 2013; for Japanese Pat. App. No. 2010-201028; 4 pages.
Japanese Second Office Action (English translation) dated Aug. 7, 2013; for Japanese Pat. App. No. 2010-201028; 3 pages.

Letter from NTD Patent and Trademark Office dated Oct. 10, 2012; for Chinese Pat. App. No. 200980106535.4; 2 pages.
Chinese First Office Action (with English translation) dated Aug. 29, 2012; for Chinese Pat. App. No. 200980106535.4; 8 pages.
Letter to NTD Patent and Trademark Office dated Dec. 11, 2012; for Chinese Pat. App. No. 200980106535.4; 8 pages.
Letter from NTD Patent and Trademark Office dated Jan. 19, 2013; for Chinese Pat. App. No. 200980106535.4; 1 page.
Response to Chinese First Office Action dated Aug. 29, 2012; for Chinese Pat. App. No. 200980106535.4; 12 pages.
Letter from NTD Patent and Trademark Office dated May 21, 2013; for Chinese Pat. App. No. 200980106535.4; 2 pages.
Chinese Second Office Action (with English translation) dated Apr. 15, 2013; for Chinese Pat. App. No. 200980106535.4; 9 pages.
Letter to NTD Patent and Trademark Agency dated Jun. 19, 2013; for Chinese Pat. App. No. 200980106535.4; 11 pages.
Letter from NTD Patent and Trademark Agency dated Jul. 11, 2013; for Chinese Pat. App. No. 200980106535.4; 1 pages.
Response to Chinese Second Office Action dated Aug. 29, 2012; for Chinese Pat. App. No. 200980106535.4; 12 pages.
Letter from Yuasa and Hara dated May 27, 2013; for Japanese Pat. App. No. 2010-547666; 2 pages.
Japanese Notice of Reasons for Rejection (English translation) for Japanese Pat. App. No. 2010-547666; 4 pages.
Email from NTD Patent and Trademark Office dated Jun. 11, 2012; for Chinese Pat. App. No. 200920783766.7; 2 pages.
Japanese First Office Action (with English translation) dated May 3, 2012; for Chinese Pat. App. No. 200920783766.7; 13 pages.
Letter to NTD Patent and Trademark Office dated Aug. 29, 2012; for Chinese Pat. App. No. 200920783766.7; 20 pages.
Letter from NTD Patent and Trademark Office dated Oct. 18, 2012; for Chinese Pat. App. No. 200920783766.7; 1 pages.
Response to Japanese First Office Action dated May 3, 2013; for Chinese Pat. App. No. 200920783766.7; 9 pages.
Letter from NTD Patent and Trademark Agency dated Feb. 6, 2013; for Chinese Pat. App. No. 200920783766.7; 2 pages.
Japanese Second Office Action dated Jan. 18, 2013; for Chinese Pat. App. No. 200920783766.7; 8 pages.
Letter to NTD Patent and Trademark Agency dated Feb. 6, 2013; for Chinese Pat. App. No. 200920783766.7; 2 pages.
Letter from NTD Patent and Trademark Agency dated Mar. 21. 2013; for Chinese Pat. App. No. 200920783766.7; 1 page.
Response to Japanese Second Office Action (with English translation) dated Jan. 18, 2013; for Chinese Pat. App. No. 200920783766. 7; 7 pages.
Chinese Notice of Completing Formalities for Patent Registration (with English translation), dated Mar. 6, 2013; for Chinese Pat. App. No. 200920783766.7; 4 pages.
Letter from Yuasa and Hara dated Aug. 16, 2013; for Japanese Pat. App. No. 2011-539582; 3 pages.
Japanese Notice of Reasons for Rejection; dated Jul. 16, 2013; for Japanese Pat. App. No. 2011-539582; 3 pages.
EP Official Communication; dated Feb. 23, 2012; for EP Pat. App. No. 10739429.8; 2 pages.
Response to EP Official Communication dated Feb. 23, 2012 for EP Pat. App. No. 10739429.8; filed on Sep. 4, 2012, 21 pages.
European Decision to Grant Patent dated Sep. 5, 2013; for European Pat. App. No. 10739429.8; 2 pages.
PCT Search Report dated Nov. 19, 2003 for PCT Pat. App. No. PCT/US03/02489; 5 pages.
PCT Search Report for PCT/US2006/000363 dated May 11, 2006.
PCT International Preliminary Report and Written Opinion on Patentability of the ISA dated Aug. 7, 2007; for PCT/US2006/000363; 9 pages.
PCT Search Report and Written Opinion of the ISA for PCT/US2008/053551; dated Jul. 15, 2008; 11 pages.
PCT International Preliminary Report on Patentability for PCT/US2008/053551; dated Oct. 8, 2009; 7 pages.
PCT Search Report of the ISA for PCT/US2009/031776 dated Oct. 23, 2009.
PCT International Preliminary Report on Patentability and Written Opinion dated Sep. 10, 2010 for PCT/US2009/031776.

(56) References Cited

OTHER PUBLICATIONS

PCT Search Report of the ISA for PCT/US2009/048237 dated Aug. 25, 2009; 2 pages.
PCT International Preliminary Report on Patentability and Written Opinion for PCT/US2009/048237 dated Feb. 10, 2011, 8 pages.
European Response to Written Opinion dated Apr. 18, 2011; for European Pat. App. No. 09789890.2; 11 pages.
PCT Search Report and Written Opinion for PCT/US2009/065044 dated Jan. 7, 2010; 11 pages.
PCT International Preliminary Report on Patentability and Written Opinion of the ISA; dated Jun. 7, 2011; for PCT Pat. App. No. PCT/US2009/065044; 7 pages.
PCT Search Report and Written Opinion of the ISA for PCT/US2010/024256 dated Aug. 11, 2010; 11 pages.
Amendment under PCT Article 19 filed on Oct. 5, 2010 in PCT/US2010/024256; 18 pages.
PCT International Preliminary Report on Patentability and Written Opinion of the ISA dated Sep. 1, 2011; for PCT Pat. App. No. PCT/US2010/024256; 9 pages.
PCT Search Report and Written Opinion of the ISA for PCT/US2010/042694 dated Sep. 27, 2010; 13 pages.
PCT International Preliminary Report on Patentability and Written Opinion of the ISA; dated Feb. 2, 2012; for PCT Pat. App. No. PCT/US2010/042694; 11 pages.
European Search Report dated Jul. 4, 2011; for European Pat. App. No. 13169661.9; 11 pages.
PCT Search Report and Written Opinion of the ISA for PCT Pat. App. No. PCT/US2012/032315; dated Jun. 22, 2012; 16 pages.
PCT Search Report and the Written Opinion of the ISA dated Jul. 17, 2013; for PCT/US2013/037065; 13 pages.
Office Action in U.S. Appl. No. 13/468,478 dated Jan. 15, 2014, 36 pages.
U.S. Appl. No. 13/946,830, filed Jul. 19, 2013, Taylor et al.
U.S. Appl. No. 14/529,577, filed Oct. 31, 2014, Foletto et al.
U.S. Appl. No. 14/529,594, filed Oct. 31, 2014, Drouin et al.
U.S. Appl. No. 14/529,606, filed Oct. 31, 2014, Foletto et al.
U.S. Appl. No. 14/529,669, filed Oct. 31, 2014, David et al.
PCT Search Report and Written Opinion of the ISA dated Dec. 19, 2014; for PCT Pat. App. No. PCT/US2014/044236; 23 pages.
U.S. Appl. No. 13/871,131, filed Apr. 26, 2013, David et al.
U.S. Appl. No. 13/748,999, filed Jan. 24, 2013, Vig et al.
U.S. Appl. No. 13/439,094, filed Apr. 4, 2012, Friedrich et al.
U.S. Appl. No. 13/946,010, filed Jul. 19, 2013, David et al.
U.S. Appl. No. 13/946,380, filed Jul. 19, 2013, Taylor et al.
U.S. Appl. No. 13/946,400, filed Jul. 19, 2013, David et al.
Bowers et al.; "Microfabrication and Process Integration of Powder-Based Permanent Magnets,"Technologies for Future Micro-Nano Manufacturing Workshop; Aug. 2011; pp. 162-165.
Kapser et al.; "Integrated GMR Based Wheel Speed Sensor for Automotive Applications;" IEEE 2007 Conference on Sensors; Oct. 2007; pp. 848-851.
Oniku et al.; "High-Energy-Density Permanent Micromagnets Formed From Heterogeneous Magnetic Powder Mixtures;" IEEE $25^{th}$ International Conference on Micro Electro Mechanical Systems, Jan. 2012; 4 pages.
International Search Report and Written Opinion dated Oct. 28, 2014 for Int'l PCT Application PCT/US2014/044991; 12 pages.
International Search Report and Written Opinion dated Nov. 4, 2014 for Int'l PCT Application PCT/US2014/044993; 13 pages.
PCT Invitation to Pay Additional Fees and Partial Search Report dated Nov. 4, 2014; for PCT Pat. App. No. PCT/US2014/044236; 7 pages.
Response filed Jun. 16, 2015; to Office Action dated Feb. 12, 2015; for U.S. Appl. No. 13/468,478; 11 pages.
Response filed Apr. 3, 2015; to Office Action dated Jan. 5, 2015; for U.S. Appl. No. 13/946,400; 13 pages.
Final Office Action dated Jun. 9, 2015; for U.S. Appl. No. 13/946,400; 17 pages.
Office Action dated Jul. 9, 2015; for U.S. Appl. No. 13/946,380; 63 pages.
Response dated Nov. 9, 2015 to Office Action dated Jul. 9, 2015; for U.S. Appl. No. 13/946,380; 26 pages.
U.S. Appl. No. 13/468,478 Final Office Action dated Sep. 16, 2015, 19 pages.
Amendment and Request for Continued Examination dated Sep. 9, 2015; for U.S. Appl. No. 13/946,400, 12 pages.
PCT International Preliminary Report on Patentability and Written Opinion of the ISA dated Jan. 28, 2016; for PCT Pat. App. No. PCT/US2014/044236; 17 pages.
U.S. Appl. No. 13/468,478 Response to Final Office Action filed Jan. 14, 2016, 18 pages.
U.S. Appl. No. 13/468,478 Request for Continued Examination filed Jan. 14, 2016, 3 pages.
Non-Final Office Action dated Nov. 19, 2015; for U.S. Appl. No. 13/946,400; 24 pages.
European Communication under Rule 71(3) EPC, Intention to Grant dated Jun. 2, 2016 corresponding to European Application No. 13722619.7; 7 Pages.
Office Action dated Jul. 14, 2016 for U.S. Appl. No. 14/529,594; 94 pages.
PCT International Preliminary Report on Patentability and Written Opinion of the ISA dated Nov. 20, 2014; for PCT Pat. App. No. PCT/US2013/037065; 11 pages.
PCT International Search Report and Written Opinion of the ISA dated Jan. 15, 2016; for PCT Pat. App. No. PCT/US2015/055236; 12 pages.
Response with RCE filed on Apr. 12, 2016 to the Final Office Action dated Dec. 15, 2015; for U.S. Appl. No. 13/946,380; 20 pages.
PCT International Search Report and Written Opinion of the ISA dated Dec. 23, 2015; for PCT App. No. PCT/US2015/055233; 12 pages.
U.S. Office Action dated May 10, 2016 corresponding to U.S. Appl. No. 13/468,478; 20 Pages.
Office Action dated Jul. 28, 2016 for U.S. Appl. No. 14/529,669; 78 pages.
International Search Report and Written Opinion of the ISA dated Aug. 3, 2016; for PCT Application No. PCT/US2015/055230; 12 pages.
Final Office Action dated Dec. 15, 2015; for U.S. Appl. No. 13/946,380; 36 pages.
PCT International Search Report and Written Opinion of the ISA dated Feb. 4, 2016; for PCT Pat. App. No. PCT/US2015/055474; 15 pages.
Final Office Action dated Jan. 4, 2017 for U.S. Appl. No. 14/529,594; 38 pages.
Final Office Action dated Jan. 9, 2017 for U.S. Appl. No. 14/529,669; 11 pages.
Final Office Action dated Jan. 12, 2017 for U.S. Appl. No. 13/946,380; 33 pages.
European Extended Search Report dated Dec. 22, 2016; for European Pat. App. No. 16193227.2; 11 pages.
Japanese Voluntary Amendment with English Claims dated Dec. 12, 2016; for Japanese Pat. App. No. 2016-528006; 7 pages.
Office Action dated Nov. 3, 2016 for U.S. Appl. No. 14/529,606; 12 pages.
Response to Office Action filed on Nov. 9, 2016 for U.S. Appl. No. 13/946,380; 19 pages.
Response to Office Action filed Jan. 27, 2017 for U.S. Appl. No. 14/529,577; 18 pages.
Response to Office Action filed Jan. 26, 2017 for U.S. Appl. No. 14/529,606; 19 pages.
Response to U.S. Final Office Action dated Oct. 20, 2016 (w/RCE) for U.S. Appl. No. 13/946,400; Response filed on Feb. 23, 2017; 17 Pages.
Voluntary Amendment dated Nov. 2, 2016 with English claims for Chinese Application No. 201480040243.6; 13 pages.
Response filed on Jan. 19, 2017 to Final Office Action dated Oct. 20, 2016; for U.S. Appl. No. 13/946,400;; 13 Pages.
Office Action dated Nov. 9, 2016 regarding U.S. Appl. No. 14/529,577; 14 pages.
Voluntary Amendment with English Claims dated Nov. 7, 2016 for Korean App. No. 10-2016-7004178; 15 Pages.

(56) References Cited

OTHER PUBLICATIONS

Response filed on Nov. 9, 2016 to the Non-Final Office Action dated Aug. 26, 2016; for U.S. Appl. No. 13/946,380; 19 pages.
Decision to Grant dated Oct. 27, 2016; for European Pat. App. No. 13722619.7; 2 pages.
Office Action dated Aug. 26, 2016 for U.S. Appl. No. 13/946,380, 40 pages.
European Response filed on Aug. 24, 2016 to the official communication dated Feb. 23, 2016; for European Pat. App. No. 14742423.8; 17 pages.
Response filed on Oct. 3, 2016 to the Office Action dated May 10, 2016; for U.S. Appl. No. 13/468,478; 17 pages.
Office Action dated Oct. 20, 2016; for U.S. Appl. No. 13/946,400; 34 pages.
Response to Office Action filed Oct. 14, 2016 for U.S. Appl. No. 14/529,594; 29 pages.
Response to Office Action dated Jul. 28, 2016 for U.S. Appl. No. 14/529,669; Response filed on Oct. 28, 2016; 18 Pages.
Final Office Action dated Oct. 20, 2016 for U.S. Appl. No. 13/946,400; 20 pages.
Japanese Office Action (with English Translation) dated Jan. 13, 2017 for Japanese Application No. 2015-511491; 11 Pages.
U.S. Final Office Action dated Feb. 10, 2017 for U.S. Appl. No. 13/468,478; 27 Pages.
U.S. Advisory Action dated Feb. 16, 2017 for U.S. Appl. No. 13/946,400; 4 Pages.
EP Response filed on Dec. 9, 2016 to Official Communication dated Oct. 14, 2016 regarding European Pat. Appl. No. 14742067.3; 23 pages.
Notice of Allowance dated Mar. 10, 2017 for U.S. Appl. No. 14/529,577; 8 pages.
Applicant-Initiated Interview Summary dated Mar. 10, 2017 for U.S. Appl. No. 13/946,400; 2 pages.
Amendment filed Mar. 30, 2017 for U.S. Appl. No. 14/529,669, 12 pages.
U.S. Non-Final Office Action dated Apr. 6, 2017 for U.S. Appl. No. 13/946,400; 36 Pages.
Response to Final Office Action filed on Mar. 31, 2017 for U.S. Appl. No. 14/529,594, 16 pages.
Response (with Amended Claims in English) to Japanese Office Action dated Feb. 13, 2017 for Japanese Application No. 2015-511491; Response filed on Apr. 11, 2017; 9 Pages.
European Search Report dated Apr. 5, 2017 for EP Pat. Appl. No. 16192498.0; 10 pages.
Request for Continued Examination filed on Apr. 11, 2017 for U.S. Appl. No. 13/946,380; 3 pages.
Amendment filed on Apr. 11, 2017 for U.S. Appl. No. 13/946,380; 18 pages.
Request for Continued Examination filed Apr. 24, 2017 for U.S. Appl. No. 14/529,669; 3 pages.
Request for Continued Examination filed on Apr. 21, 2017 for U.S. Appl. No. 14/529,606; 3 pages.
Preliminary Amendment filed on Apr. 21, 2017 for U.S. Appl. No. 14/529,606; 12 pages.
Response to U.S. Final Office Action dated Feb. 10, 2017 for U.S. Appl. No. 13/468,478; Response filed on May 3, 2017; 9 Pages.
Notice of Allowance dated May 15, 2017 for U.S. Appl. No. 13/468,478; 15 Pages.
Notice of Allowance dated May 10, 2017 for U.S. Appl. No. 14/529,594; 8 pages.
Non-final Office Action dated May 19, 2017 for U.S. Appl. No. 14/529;606; 11 pages.
Notice of Allowance dated May 18, 2017 for U.S. Appl. No. 14/529,669; 8 pages.
Office Action dated May 19, 2017 for U.S. Appl. No. 13/946,380; 20 pages.
Request for Continued Examination for U.S. Appl. No. 13/468,478; Filed on Jun. 5, 2017; 3 Pages.
Japanese Office Action (with English Translation) dated May 18, 2017 for Japanese Application No. 2015-511491; 8 Pages.

Response to Office Action filed on Jun. 30, 2017 for U.S. Appl. No. 13/946,400; 12 pages.
Response to Office Action filed on Jun. 29, 2017 for U.S. Appl. No. 14/529,669; 11 pages.
Japanese Office Action (with English Translation) dated May 18, 2017 for Japanese Application No. 2015-511491; 5 Pages.
Notice of Allowance dated Jul. 13, 2017 for U.S. Appl. No. 13/946,380; 11 pages.
U.S. Appl. No. 15/624,898, filed Jun. 16, 2017, Drouin et al.
Preliminary Amendment filed on Jun. 16, 2017 for U.S. Appl. No. 15/624,898; 15 pages.
Notice of Allowance dated Aug. 4, 2017 for U.S. Appl. No. 14/529,606; 9 pages.
A.A. Thornton response to official communication dated May 22, 2017 and filed on Nov. 17, 2017 regarding Div. EP Patent Application No. 16192498.0; 7 pages.
Amended Claims in response to official communication filed on Nov. 17, 2017 regarding Div. EP Patent Application No. 16192498.0; 7 pages.
Response to Japanese Office Action (with English claims) dated Oct. 3, 2017 for Japanese Application No. 2016-528006; Response filed Dec. 26, 2017; 8 Pages.
Response to U.S. Final Office Action dated Oct. 5, 2017 for U.S. Appl. No. 13/946,400; Response filed Jan. 5, 2018; 11 Pages.
Korean Office Action (with English Translation) dated Dec. 20, 2017 corresponding to Korean Appl. No. 10-2014-7032857; 14 Pages.
U.S. Non-Final Office Action dated Jan. 9, 2018 corresponding to U.S. Appl. No. 15/709,739; 12 Pages.
Response to Notice to File Corrected Application Papers dated Aug. 28, 2017 and filed on Aug. 29, 2017 for U.S. Appl. No. 13/946,380; 3 pages.
U.S. Appl. No. 15/606,352, filed May 26, 2017, Latham et al.
U.S. Appl. No. 15/606,358, filed May 26, 2017, Latham et al.
U.S. Appl. No. 15/606,325, filed May 26, 2017, Latham et al.
U.S. Appl. No. 15/606,332, filed May 26, 2017, Latham et al.
U.S. Appl. No. 15/709,739, filed Sep. 20, 2017, Pepka et al.
Response to Official Communication dated Mar. 13, 2017 for European Application No. 16193227.2; Response filed Oct. 2, 2017; 7 pages.
U.S. Final Office Action dated Oct. 5, 2017 for U.S. Appl. No. 13/946,400; 39 pages.
EP Reply to Official Communication filed on Nov. 29, 2017 for EP Pat. Appl. No. 15787111.2; 2 pages.
EP Amended Specification filed on Nov. 29, 2017 for EP Pat. Appl. No. 15787111.2; 2 pages.
EP Amended Claims filed on Nov. 29, 2017 for EP Pat. Appl. No. 15787111.2; 13 pages.
Appeal Brief dated Sep. 19, 2017 from Japanese Application No. 2015-511491 with English translations; 14 Pages.
Pre-Trial Report dated Nov. 2, 2017 from Japanese Application No. 2015-511491 with English translations and Claims on File; 7 Pages.
Korean Office Action with English Translation dated Nov. 22, 2017 for Korean Application No. 10-2016-7004178; 17 Pages.
Examination Report dated Mar. 8, 2018 for EP Appl. No. 15791066.2; 4 pages.
Japanese Offfice Action (with English Translation) dated May 16, 2018 for Japanese Application No. 2015-511491; 9 Pages.
Korean Office Action (with English Translation) dated May 30, 2018 for Korean Application No. 10-2016-7004178; 11 pages.
Response to U.S. Final Office Action dated Oct. 5, 2017 for U.S. Appl. No. 13/946,400; Response filed on Feb. 27, 2018; 14 Pages.
Response to Official Communication filed Dec. 21. 2017 for EP Pat. Appl. No. 15787099.9; 3 pages.
Amended Claims filed in Response to Official Communication filed Dec. 21, 2017 for EP Pat. Appl. No. 15787099.9; 7 pages.
Response to U.S. Non-Final Office Action dated Jan. 26, 2018 for U.S. Appl. No. 15/655,135; Response filed Apr. 3, 2018; 20 pages.
U.S. Appl. No. 15/655,135, filed Jul. 20, 2017, Taylor et al.
U.S. Non-Final Office Action dated Jan. 5, 2015 for U.S. Appl. No. 13/946,400; 23 Pages.
Response to U.S. Non-Final Office Action dated Nov. 19, 2015 for U.S. Appl. No. 13/946,400; Response filed Feb. 17, 2016; 11 Pages.

(56) References Cited

OTHER PUBLICATIONS

PCT International Preliminary Report and Written Opinion dated Jan. 28, 2016 for International Application No. PCT/US2014/044993; 9 Pages.
Response to U.S. Non-Final Office Action dated Jan. 15, 2014 for U.S. Appl. No. 13/468,478; Response filed Jun. 12, 2014; 11 Pages.
U.S. Final Office Action dated Jul. 17, 2014 for U.S. Appl. No. 13/468,478; 13 Pages.
Response to U.S. Final Office Action dated Jul. 17, 2014 for U.S. Appl. No. 13/468,478; Response filed Jan. 19, 2015; 12 Pages.
U.S. Non-Final Office Action dated Feb. 12, 2015 for U.S. Appl. No. 13/468,478; 12 Pages.
Notice of Allowance dated Jul. 25, 2017 for U.S. Appl. No. 13/468,478; 7 Pages.
PCT International Preliminary Report and Written Opinion dated May 11, 2017 for International Application No. PCT/US2015/055233; 8 Pages.
Notice of Allowance dated Apr. 20, 2017 for U.S. Appl. No. 14/529,669; 8 Pages.
Notice of Allowance dated Mar. 16, 2017 for U.S. Appl. No. 14/529,606; 9 Pages.
PCT International Preliminary Report and Written Opinion dated May 11, 2017 for International Application No. PCT/US2015/055236; 9 Pages.
Response to U.S. Non-Final Office Action dated Jul. 14, 2016 for U.S. Appl. No. 14/529,594; Response filed Oct. 14, 2016; 29 Pages.
Intention to Grant dated Feb. 28, 2018 for European Application No. 15787111.2; 7 Pages.
PCT International Preliminary Report and Written Opinion dated May 11, 2017 for International Application No. PCT/US2015/055474; 12 Pages.
PCT International Preliminary Report and Written Opinion dated Jan. 28, 2016 for International Application No. PCT/US2014/044991; 9 Pages.
Daughton; "Spin-Dependent Sensors;" Proceedings of the IEEE, vol. 91, No. 5; May 2003; 6 Pages.
Communication under Rule 71(3) EPC for EP Pat. Appl. No. 15787111.2 dated Feb. 28, 2018; 7 pages.
Allowed specification for EP Pat. Appl. No. 15787111.2 dated Nov. 29, 2017; 87 pages.
Korean Response (with English Language Summary) dated Jan. 19, 2018 for Korean Application No. 10-2016-7004178; 25 Pages.
Chinese Office Action (w/English Translation) dated Feb. 1, 2018 for Chinese Application No. 201480040243.6; 26 Pages.
Notice of Allowance dated Apr. 4, 2018 for U.S. Appl. No. 13/946,400; 11 pages.
A.A. Thornton letter filed Dec. 15, 2017 in response to EPO communication under Rule 161 and 162EPC for EP Pat. Appl. No. 15791066.2; 2 pages.
Amended claims filed on Dec. 15, 2017 in response to EPO communication under Rule 161 and 162EPC for EP Pat. Appl. No. 15791066.2; 5 pages.
Japanese Petition (with Machine English Translation) filed Jan. 24, 2018 for Japanese Application No. 2015-511491; 10 Pages.
Response (with English Translation) to Korean Notice of Reasons for Refusal dated Dec. 20, 2017 for Korean Application No. 10-2014-7032857; Response filed Feb. 14, 2018; 47 Pages.
Response to EPO Communication under Rules 161 and 162 EPC filed on Dec. 21, 2017 for EP Pat. Appl. No. 15853626.8; 2 pages.
Amended Claims in response to EPO Communication under Rules 161 and 162 EPC filed on Dec. 21, 2017 for EP Pat. Appl. No. 16853626.8; 7 pages.
Non-final office action dated Jan. 26, 2018 for U.S. Appl. No. 15/655,135; 50 pages.
Japanese Office Action dated Dec. 17, 2018 for Japanese Application No. 2015-511491; 10 pages.
Chinese Response (w/English Claims and Remarks) filed Dec. 24, 2018 for Chinese Application No. 201480040243.6; 14 pages.
Office Action dated Nov. 28, 2018 for U.S. Appl. No. 15/624,898; 35 Pages.

Response filed on Nov. 14, 2018 for Japanese Application No. 2015-511491 with English Translation; 11 Pages.
Response filed on Nov. 14, 2018 for Japanese Application No. 2017-178549 with English Translation; 13 Pages.
Non-Final Office Action dated Nov. 8, 2018 for U.S. Appl. No. 15/606,325; 24 Pages.
A.A. Thornton letter dated Nov. 26, 2018 in to response Official Communication dated Jul. 9, 2018 for EP Pat. Appl. No. 15853626.8; 4 pages.
Amended Claims filed on Nov. 26, 2018 for EP Pat. Appl. No. 15653626,8; 4 pages.
U.S. Non-Final Office Action dated Jan. 24, 2019 for U.S. Appl. No. 15/606,358; 27 pages.
Response to Examination report dated May 28, 2018 for European Application No. 15787099.9 as filed on Sep. 17, 2018; 3 Pages.
Amended claims for European Application No. 15787099.9 as filed on Sep. 17, 2018; 4 Pages.
Replacement p. 5 of specification for European Application No. 15787099.9 as filed on Sep. 17, 2018; 1 Page.
New p. 5A of specification for European Application No. 15787099.9 as filed on Sep. 17, 2018; 1 Page.
U.S. Appl. No. 16/136,844, filed Sep. 20, 2018, David et al.
PCT International Search Report and Written Opinion dated Jul. 20, 2018 for International Application No. PCT/US2018/028572; 14 pages.
PCT International Search Report and Written Opinion dated Aug. 10, 2018 for International Application No. PCT/US2018/028816; 23 pages.
Non-Final Office Action dated Oct. 5, 2018 for U.S. Appl. No. 16/029,826; 22 pages.
Japanese Notice of Allowance (with English Translation) dated Sep. 28, 2018, for Japanese Application No. 2016-528006; 5 Pages.
Korean Notice of Allowance (with English Translation) dated Oct. 2, 2018, for Korean Application No. 10-2016-7004178; 5 Pages.
European Response dated Sep. 17, 2018 for European Application No. 15787099.9; 9 pages.
Final Office Action dated Oct. 25, 2018 for U.S. Appl. No. 15/709,739; 14 Pages.
Second Office Action dated Oct. 9, 2018 for Chinese Application No. 201480040243.6 with English Translations; 23 Pages.
Japanese Office Action dated Aug. 2, 2018 for Japanese Application No. 2017-178549; 9 pages.
Notice of Allowance dated Jul. 6, 2018 for U.S. Appl. No. 13/946,400; 12 pages.
U.S. Final Office Action dated Jul. 26, 2018 for U.S. Appl. No. 15/655,135; 38 pages.
Restriction Requirement dated Sep. 7, 2018 for U.S. Appl. No. 15/624,898; 7 pages.
Response to U.S. Final Office Action dated Jul. 26, 2018 for U.S. Appl. No. 15/655,135; Response filed Oct. 11, 2018; 21 pages.
U.S. Non-Final Office Action dated Nov. 8, 2018 for U.S. Appl. No. 15/606,325; 24 pages.
Response to Korean Office Action dated May 30, 2018 for Korean Application No. 10-2016-7004178; Response (with English claims) filed Jul. 19, 2018; 41 pages.
Japanese Office Action (with English translation) dated Jun. 1, 2018 for Japanese Application No. 2016-528006; 7 pages.
Response to U.S. Non-Final Office Action dated Jan. 9, 2018 for U.S. Appl. No. 15/709,739; Response filed Jun. 25, 2018; 11 pages.
Korean Notice of Allowance (with English translation and allowed claims) dated Jun. 29, 2018 for Korean Application No. 10-2014-7032857; 8 pages.
Response to Chinese Office Action dated Feb. 1, 2018 for Chinese Application No. 201480040243.6; Response filed Jun. 14, 2018; 11 pages.
English translations of Claims on File dated Sep. 20, 2018 for Japanese Application No. 2017-522906; 7 Pages.
Instruction Letter to Foreign Associate dated Jul. 30, 2018 for Japanese Application No. 2017-522906; 2 Pages.
Letter from Foreign Associate dated Sep. 20, 2018 reporting voluntary amendment filed for Japanese Application No. 2017-522906; 2 Pages.

(56) References Cited

OTHER PUBLICATIONS

Examination Report dated May 28, 2018 for EP Pat. Appl. No. 15787099.9-1022; 7 pages.
Response to Office Action dated Nov. 26, 2018 and filed on Jan. 11, 2019 for U.S. Appl. No. 15/624,898; 17 pages.
Response to Final Office Action dated Jul. 26, 2018 for U.S. Appl. No. 15/655,135, filed Oct. 11, 2018; 21 pages.
Japanese Office Action with English Translations for Japanese Application No. 2017-178549 dated Jul. 30, 2018; 4 Pages.
Response to Japanese Office Action with English translations of Amended Claims for Japanese Application No. 2016-528006 as filed on Aug. 3, 2018; 7 Pages.
Amended p. 5 Description with tracked changes and New p. 5a Description as filed on Jul. 13, 2018 for EP Application No. 15791066.2; 2 Pages.
Amended Description with tracked changes as filed on Jul. 13, 2018 for EP Application No. 15791066,2; 11 Pages.
Amended Claims with tracked changes as filed on Jul. 13, 2018 for EP Application No. 15791066.2; 4 Pages.
Response to the Official Communication dated Mar. 8, 2018 for EP Application No. 15791066.2 as filed on Jul. 13, 2018; 2 Pages.
Communication pursuant to Article 94(3) EPC dated Jul. 9, 2018 for EP Application No. 15853626.8; 4 Pages.
Communication under Rule 71(3) EPC dated Oct. 10, 2018 for International Application No. 15791066.2; 7 Pages.
Allowed Specification dated Oct. 10, 2018 for International Application No. 15791066.2; 102 Pages.
PCT International Search Report and Written Opinion dated Nov. 23, 2018 for International Application No. PCT/US2018/028475; 17 pages.
PCT International Search Report and Written Opinion dated Nov. 30, 2018 for International Application No. PCT/US2018/028821; 12 pages.
Japanese Notice of Allowance (with English Translation of Allowed Claims) dated May 16, 2019 for Japanese Application No. 2015-511491; 6 Pages.
Response to U.S. Non-Final Office Action dated Mar. 8, 2019 for U.S. Appl. No. 15/709,739; Response filed Jun. 10, 2019; 15 Pages.
U.S. Final Office Action dated May 16, 2019 for U.S. Appl. No. 15/606,325; 24 Pages.
Amendment under 37 C.F.R. §1.114 filed on Apr. 10, 2019 for U.S. Appl. No. 15/624,898; 19 pages.
Response to Office Action filed on Jun. 22, 2017 for U.S. Appl. No. 13/946,380; 8 pages.
Response to Final Office Action dated Oct. 25, 2018 for U.S. Appl. No. 15/709,739, filed Jan. 18, 2019; 10 Pages.
Response to U.S. Non-Final Office Action dated Nov. 8, 2018 for U.S. Appl. No. 15/606,325; Response filed Feb. 7, 2019; 14 pages.
Response to U.S. Non-Final Office Action dated Oct. 5, 2018 for U.S. Appl. No. 16/029,826; Response filed Feb. 1, 2019; 10 pages.
Non-Final Office Action dated Jun. 13, 2019 for U.S. Appl. No. 15/606,332; 24 Pages.
Response filed on Jun. 6, 2019 for Chinese Application No. 201480040243.6; 17 Pages.
Final Office Action dated Feb. 14, 2019 for U.S. Appl. No. 15/624,898; 30 pages.
Response to Office Action filed on Jul. 5, 2017 for U.S. Appl. No. 14/529,606; 13 pages.
Yuasa and Hara Letter dated Apr. 1, 2019 for JP Pat. Appl. No. 2017-522907; 3 pages.
Yuasa and Hara Notice for Reasons for Rejection filed on Mar. 1, 2019 for JP Pat. Appl. No. 2017-522907; 5 pages.
Yuasa and Hara Claims Now on File filed on Mar. 1, 2019 for JP Pat. Appl. No. 2017-522907; 12 pages.
U.S. Non-Final Office Action dated Apr. 26, 2019 for U.S. Appl. No. 15/606,352; 15 pages.
Intention to Grant dated Apr. 25, 2019 for EP Pat. Appl. No. 15853626.8-1022; 7 pages.
Allowed Specification dated Jul. 7, 2016 for EP Pat. Appl. No. 15853626.8; 104 pages.
Non-Final Office Action dated Mar. 8, 2019 for U.S. Appl. No. 15/709,739; 15 Pages.
Response filed on Mar. 14, 2019 for Japanese Application No. 2015-511491 with English Machine Translation; 12 Pages.
Response filed on May 29, 2019 for Japanese Patent Application No. 2017-522907 with English Translation; 40 Pages.
Notice of Allowance dated Jun. 10, 2019 for Japanese Patent Application No. 2017-522908 with English Translation of Allowed Claims; 9 Pages.
Response to Non-Final Office Action dated Apr. 26, 2019 for U.S. Appl. No. 15/606,352, filed Jul. 3, 2019; 11 Pages.
DCMD Instruction letter dated Feb. 13, 2019 for KR Pat. Appl. No. 10-2016-7004180; 2 pages.
21st Century Letter dated Mar. 14, 2019 regarding Voluntary Amendment and Substantive Examination for KR Pat. Appl. No. 10-2016-7004180; 1 page.
21st Century Listing of Pending Claims filed on Mar. 14, 2019 regarding Voluntary Amendment and Substantive Examination for KR Pat. Appl. No. 10-2016-7004180; 13 pages.
Notice of Allowance dated Apr. 16, 2019 for Japanese Application No. 2017-178549 with English Translation of Allowed claims; 8 Pages.
Office Action dated Mar. 22, 2019 for Chinese Application No. 201480040243.6 with English Translation; 22 Pages.
Response to Non-Final Office Action dated Jan. 24,2019 for U.S. Appl. No. 15/606,358, filed Apr. 17, 2019; 12 Pages.
Office Action dated Jul. 10, 2019 for U.S. Appl. No. 15/658,757: 23 pages.
Notice of Intention to Grant dated May 27, 2019 for EP Pat. Appl. No. 15787099.9; 7 pages.
Allowed Specification dated May 6, 2016 for EP Pat. Appl. No. 15787099.9; 71 pages.
Final Office Action dated Sep. 19, 2019 for U.S Appl. No. 16/029,826; 22 pages.
Non-Final Office Action dated Aug. 22, 2019 for U.S. Appl. No. 15/606,358; 32 pages.
Response to Office Action dated May 16, 2019 for U.S. Appl. No. 15/606,325 as filed on Aug. 14, 2019; 15 pages.
Response to Office Action dated Jun. 13, 2019 for U.S. Appl. No. 15/606,332 as filed on Aug. 26, 2019; 18 pages.

* cited by examiner

METHODS AND APPARATUS FOR MAGNETIC SENSOR HAVING AN INTEGRATED COIL OR MAGNET TO DETECT A NON-FERROMAGNETIC TARGET

FIELD

This disclosure relates to magnetic field sensors and, more particularly, to magnetic field sensors having an integrated coil or magnet.

BACKGROUND

There are a variety of types of magnetic field sensing elements, including, but not limited to, Hall Effect elements, magnetoresistance elements, and magnetotransistors. As is also known, there are different types of Hall Effect elements, for example, planar Hall elements, vertical Hall elements, and circular vertical Hall (CVH) elements. As is also known, there are different types of magnetoresistance elements, for example, anisotropic magnetoresistance (AMR) elements, giant magnetoresistance (GMR) elements, tunneling magnetoresistance (TMR) elements, Indium antimonide (InSb) elements, and magnetic tunnel junction (MTJ) elements.

Hall Effect elements generate an output voltage proportional to a magnetic field strength. In contrast, magnetoresistance elements change resistance in proportion to a magnetic field. In a circuit, an electrical current can be directed through the magnetoresistance element, thereby generating a voltage output signal proportional to the magnetic field.

Magnetic field sensors, which use magnetic field sensing elements, are used in a variety of devices including current sensors that sense a magnetic field generated by a current carried by a current-carrying conductor, magnetic switches (also referred to herein as a proximity detector) that sense the proximity of a ferromagnetic or magnetic object, rotation detectors that sense passing ferromagnetic articles, for example, gear teeth, and magnetic field sensors that sense magnetic field or magnetic flux densities of a magnetic field.

SUMMARY

In an embodiment, a magnetic field sensor includes a magnetic source configured to provide a magnetic field to induce an eddy current in a non-ferromagnetic target, and a magnetic field sensing element configured to detect the magnetic field as a result of the eddy current. The magnetic field provided by the magnetic source can be a static (i.e. DC) field or a changing (i.e. non-DC) field.

In another embodiment, a method of detecting a magnetic field comprises placing a magnetic source in proximity to a non-ferromagnetic target. The magnetic source produces a magnetic field to induce an eddy current in the target, and a magnetic field sensing element detects the magnetic field as a result of the eddy current.

In another embodiment, a magnetic field sensor comprises a magnetic source configured to provide a magnetic field, and a magnetic field sensing element configured to detect changes in the magnetic field due to changes in an eddy current induced by the magnetic field.

BRIEF DESCRIPTION OF THE DRAWINGS

The figures aid in explanation of the disclosed technology and illustrate various exemplary embodiments. They are not intended to limit the scope of the invention, nor are they intended to present every possible embodiment. Like numbers in the figures denote like elements.

DETAILED DESCRIPTION

Figure 1:
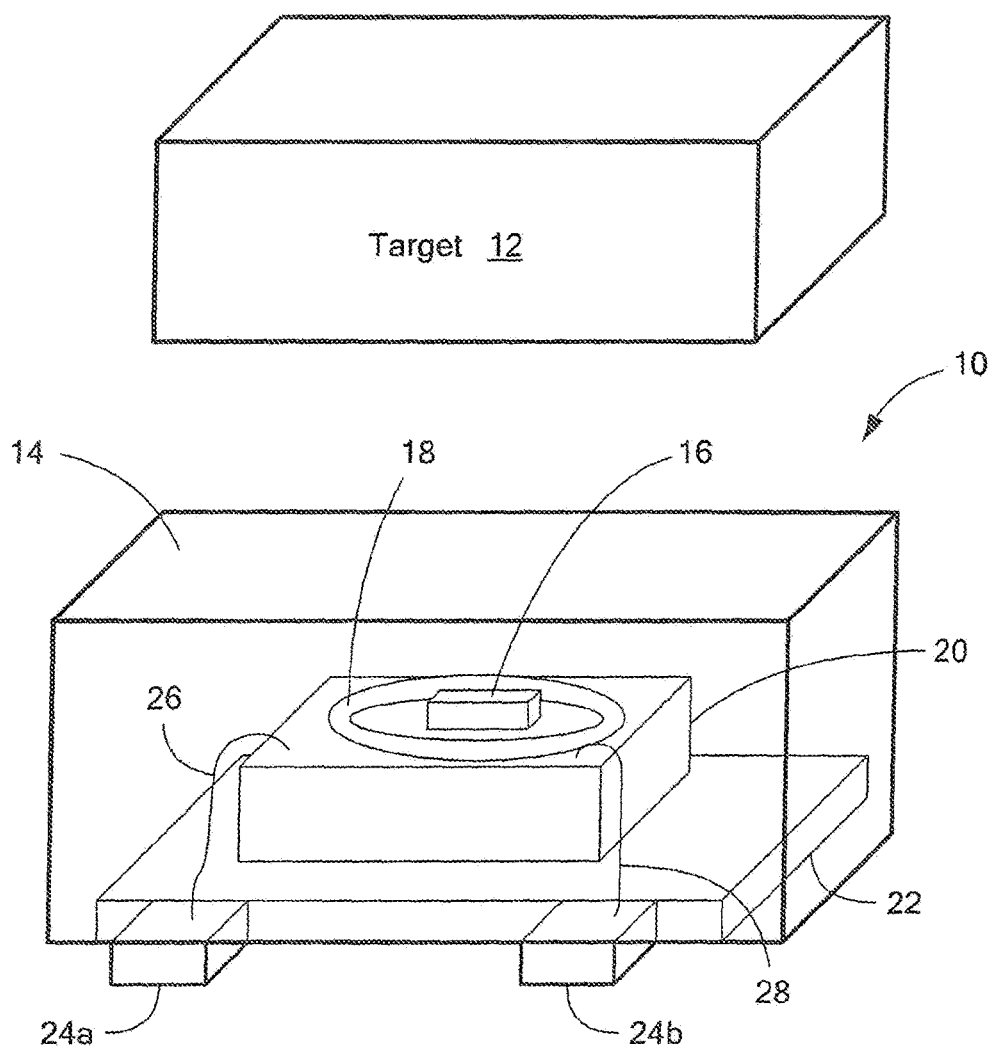
FIG. 1 is a diagram of an embodiment of a magnetic sensor having an integrated coil.

Before describing the present invention, some information is provided. As used herein, the term "magnetic field sensing element" is used to describe a variety of electronic elements that can sense a magnetic field. The magnetic field sensing element can be, but is not limited to, a Hall Effect element, a magnetoresistance element, or a magnetotransistor. As is known, there are different types of Hall Effect elements, for example, a planar Hall element, a vertical Hall element, and a Circular Vertical Hall (CVH) element. As is also known, there are different types of magnetoresistance elements, for example, a semiconductor magnetoresistance element such as Indium Antimonide (InSb), a giant magnetoresistance (GMR) element, an anisotropic magnetoresistance element (AMR), a tunneling magnetoresistance (TMR) element, and a magnetic tunnel junction (MTJ). The magnetic field sensing element may be a single element or, alternatively, may include two or more magnetic field sensing elements arranged in various configurations, e.g., a half bridge or full (Wheatstone) bridge. Depending on the device type and other application requirements, the magnetic field sensing element may be a device made of a type IV semiconductor material such as Silicon (Si) or Germanium (Ge), or a type III-V semiconductor material like Gallium-Arsenide (GaAs) or an Indium compound, e.g., Indium-Antimonide (InSb).

As is known, some of the above-described magnetic field sensing elements tend to have an axis of maximum sensitivity parallel to a substrate that supports the magnetic field sensing element, and others of the above-described magnetic field sensing elements tend to have an axis of maximum sensitivity perpendicular to a substrate that supports the magnetic field sensing element. In particular, planar Hall elements tend to have axes of sensitivity perpendicular to a substrate, while metal based or metallic magnetoresistance elements (e.g., GMR, TMR, AMR) and vertical Hall elements tend to have axes of sensitivity parallel to a substrate.

As used herein, the term "magnetic field sensor" is used to describe a circuit that uses a magnetic field sensing element, generally in combination with other circuits. Magnetic field sensors are used in a variety of applications, including, but not limited to, an angle sensor that senses an angle of a direction of a magnetic field, a current sensor that senses a magnetic field generated by a current carried by a current-carrying conductor, a magnetic switch that senses the proximity of a ferromagnetic object, a rotation detector that senses passing ferromagnetic articles, for example, magnetic domains of a ring magnet or a ferromagnetic target (e.g., gear teeth) where the magnetic field sensor is used in combination with a back-biased or other magnet, and a magnetic field sensor that senses a magnetic field density of a magnetic field. As used herein, the term "target" is used to describe an object to be sensed or detected by a magnetic field sensor or magnetic field sensing element.

FIG. 1 is a diagram of an exemplary embodiment of a magnetic field sensor 10 and a target 12. Magnetic field sensor 10 may include a package 14, sensing element 16 (transducer), and coil 18. Also included are a semiconductor die or integrated circuit 20, lead frame 22, and leads 24a and 24b. Wire bonds 26 and 28 couple die 20 to leads 24a and 24b. In other embodiments the die 20 may be coupled to the leads 24a and 24b using other standard packaging methods, including but not limited to solder bumps, solder balls, or pillar bumps. In other embodiments the die may be attached, for example, in a flip-chip or chip-on-lead configuration.

In an embodiment, target 12 produces or provides a magnetic field. For example, in embodiments, target 12 comprises a hard ferromagnetic target that produces a magnetic field. Alternatively, target 12 can be any type of material that produces a magnetic field including, but not limited to, an electromagnet or other type of circuit. In embodiments, target 12 may also comprise a non-ferromagnetic material capable of having eddy currents induced therein. Target 12 may also comprise a soft ferromagnetic material that changes the magnitude and or direction of a magnetic field near or in proximity to the target.

Package 14 can be any type of chip or integrated circuit package known in the art, including, but not limited to a plastic package, ceramic package, a glass sealed ceramic package, a low-temperature co-fired ceramic, or a chip-on-board encapsulant. Semiconductor die 20 may comprise one or more integrated circuits that drive coil 18 and sensing element 16.

In some embodiments, coil 18 produces a magnetic field. Coil 18 would be a coil of conductive material that, when energized with a current flowing through the material, induces a magnetic field. Integrated circuit 20 may be configured to drive a changing current through coil 18 resulting in a changing magnetic field produced by coil 18. The changing current may be an alternating current, a ramped current, a pulsed current, transient current, or any type of changing current that causes coil 18 to produce a similarly changing, i.e. complementary, magnetic field. The changing magnetic field produced by coil 18 may have sufficient magnitude to intersect the body of, and/or induce eddy currents in, target 12.

As shown in FIG. 1, coil 18 is adjacent to integrated circuit 20. However, this is not a requirement. In various embodiments, coil 18 may be placed in any location that allows the magnetic field produced by coil 18 to generate eddy currents in target 12 and to be detected by sensing element 16. Accordingly, coil 18 may be placed within package 14, on the surface of integrated circuit 20, outside of package 14, on the surface of package 14, on a separate substrate within package 14 that is independent of integrated circuit 20, etc.

Coil 18 may also be independent of package 14 and may, for example, be mounted separately from package 14. Coil 18 may be encapsulated in its own package. In embodiments, if coil 18 is separate from package 14, coil 18 may be electrically coupled to integrated circuit 20 via leads such as leads 24a and 24b. In other embodiments, coil 20 may be electrically coupled to a separate circuit that can drive current through coil 18 to produce the magnetic field. In other embodiments where a static, slowly changing, or near-constant magnetic field is desired, the coil 18 may be replaced with a hard ferromagnetic material (i.e., a permanent magnet). The hard ferromagnetic material may also be placed in any location that allows the ferromagnetic material to be detected by sensing element 16. Accordingly, the ferromagnetic material may be placed within package 14, on the surface of integrated circuit 20, outside of package 14, on the surface of package 14, on a separate substrate within package 14 that is independent of integrated circuit 20, etc. The ferromagnetic material may also be independent of package 14 and may, for example, be mounted separately from package 14.

Sensing element 16 may be a magnetic field sensing element, or any other type of circuit that can detect a magnetic field and produce an electrical signal in response to the detected magnetic field. The strength or magnitude of the signal may be proportional to the strength or magnitude of the detected magnetic field. In an embodiment, sensing element 16 is a Hall Effect element, a magnetoresistive element or circuit, a giant magnetoresistive (GMR) element or circuit, etc.

In operation, sensing element 16 will detect the magnetic field produced by coil 18 and be affected by the presence of target 12. In the absence of target 12, the detected magnetic field (and thus the resulting signal produced by sensing element 16) will have a known value. When this known value is detected, it may indicate the absence of target 12.

As target 12 moves relative to sensor 10, it affects the magnetic field generated by coil 18 and detected by sensing element 16. Recall that target 12 may produce its own magnetic field. Thus, as target 12 approaches sensor 10, the magnetic field produced by target 12 combined with the magnetic field produced by coil 18. Thus, the presence of target 12 causes perturbations or alterations to the known value of the magnetic field produced by coil 18. These perturbations can be detected by sensing element 16. For example, magnetic flux detected by sensing element 16 is a vector sum of the magnetic field produced by target 12 and the magnetic field produced by coil 18. Accordingly, the signal produced by sensing element 16 represents a combination of the two magnetic fields, i.e. the magnitude of the combined magnetic fields. In embodiments, target 12 may be positioned to enhance the effect that it has on the magnetic field produced by coil 18. For example, to increase the additive effect of the magnetic fields, target 12 may be positioned so that its magnetic field vector is in-line with (i.e. in the same or opposite direction to, and/or aligned with) the magnetic field vector of coil 18 and/or so that target 12 is as close as possible to coil 18

Integrated circuit 20 may compare the magnitude of the detected magnetic field to the expected value of the magnetic field produced by coil 18. If the measured value differs from the expected value, it may indicate the presence or proximity of target 12. In embodiments, integrated circuit can also detect the relative distance of target 12. For example, the magnetic field of target 12 can be aligned so that, the more closely target 12 approaches sensor 10, the greater affect the magnetic field produced by target 12 has on the magnetic field produced by coil 18. Thus, as target 12 approaches sensor 10, it will create a greater difference between the measured magnetic field and the expected magnetic field. As this difference changes, sensor 10 can indicate a relative distance between target 12 and sensor 10.

Based on the measured, combined magnetic field, sensor 10 may also detect presence or absence of the target.

In an embodiment, target 12 may move toward and/or away from sensor 10 during operation. By measuring the magnetic field at sensing element, sensor 10 can detect the presence and/or proximity of target 12. In an embodiment, target 12 may be a feature (such as a tooth) on a rotating wheel or gear. As the teeth pass by sensor 10, sensor 10 can create a signal (e.g. via pins 24a and/or 24b) indicating whether a tooth or valley (i.e. gap) in the gear is adjacent to sensor 10. If a tooth is present, sensor 10 can also indicate a relative distance between the tooth and sensor 10. For example, the signal produced by sensor 10 may change in amplitude based on the sensed proximity of the tooth. Additionally, if no tooth is present, sensor 10 may indicate a relative distance (e.g. a relative depth) of the gap based on the amplitude of the signal. Of course, the signal produced by sensor 10 may be analog, digital, or switched. If the signal is switched, a high output may indicate the presence of target 12 (or a tooth thereon) and a low output may indicate the absence of target 12, or vice versa.

Figure 2:
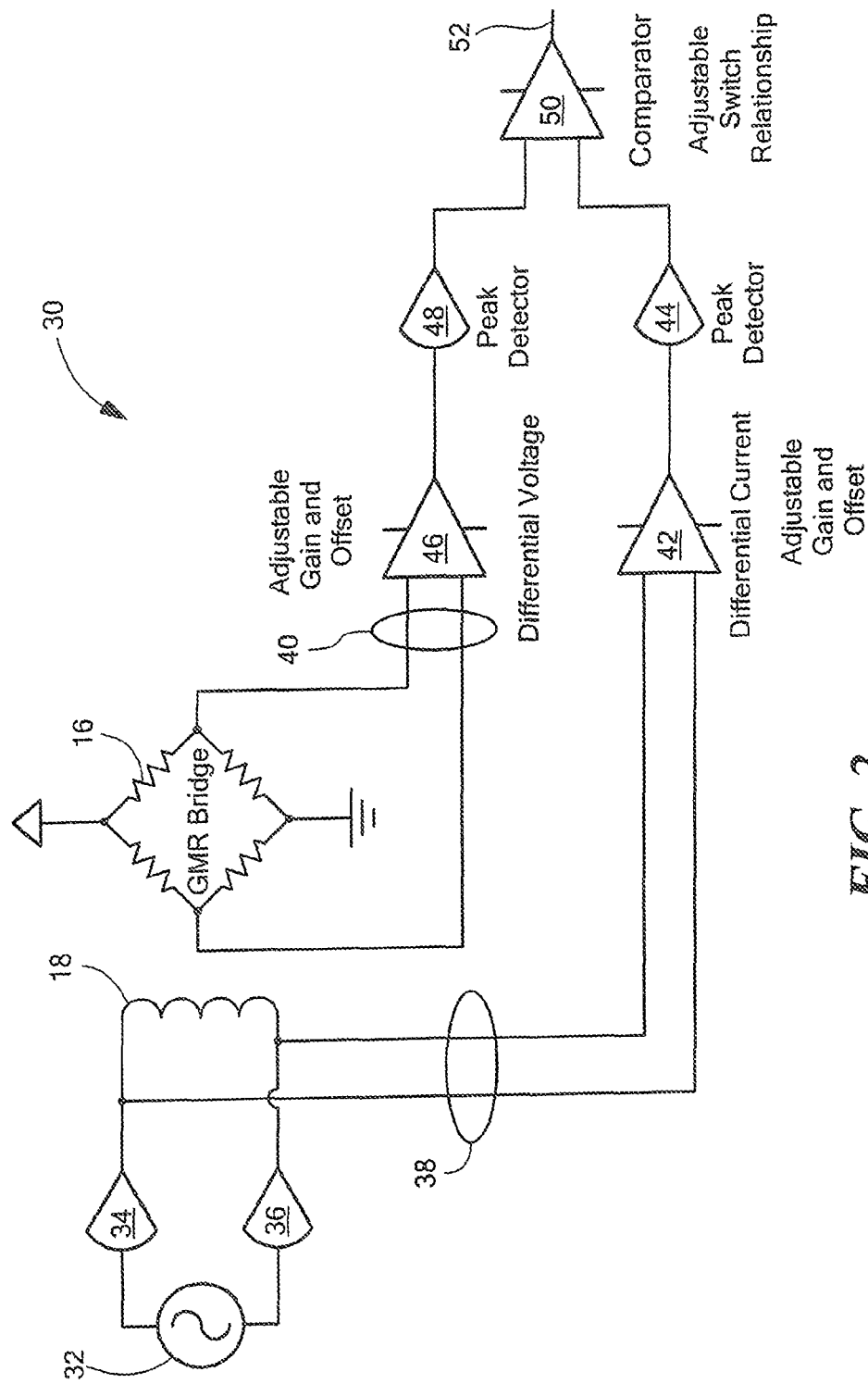
FIG. 2 is a circuit diagram of a magnetic sensor system.

Turning to FIG. 2, an example of a circuit 30 for detecting speed, direction, and/or proximity of target 12 is shown. An adjustable, changing current source 32 controls current drivers 34 and 36, which drive coil 18 and produce a differential current through signal lines 38. The changing current source may be an AC source, a ramped current source, a switched current source, a pulsed current source, a transient current source, or any other current source that creates a current that changes in magnitude over time. The current through coil 18 produces a changing magnetic field which is detected by sensing element 16. (In FIG. 2, sensing element 16 is shown as a giant-magnetoresistive (GMR) bridge). Sensing element 16 produces a differential voltage signal on signal lines 40. A differential current amplifier 42 amplifies the differential current applied to the coil 18 for coupling to a peak detector 44. A differential voltage amplifier 46 receives the differential voltage signal from sensing element 16 for coupling to a peak detector 48. Comparator 50 compares the signals from peak detectors 44 and 48 and produces an output signal 52.

The current produced by coil drivers 34 and 36, as well as the outputs of amplifiers 46 and 42 can be adjusted. Thus, in the absence of target 12, the differential current on signal lines 38 will be a known value and the differential voltage produced by sensing element 16 on signal lines 40 will be a known value. As target 12 moves relative to sensing element 16, the magnetic field affected by target 12 may affect the differential voltage on signal lines 40. This change can be compared to the known value on signal lines 38. Thus, the presence and/or proximity of target 12 can change the output of amplifier 46, peak detector 48, and/or comparator 50.

Figure 3:
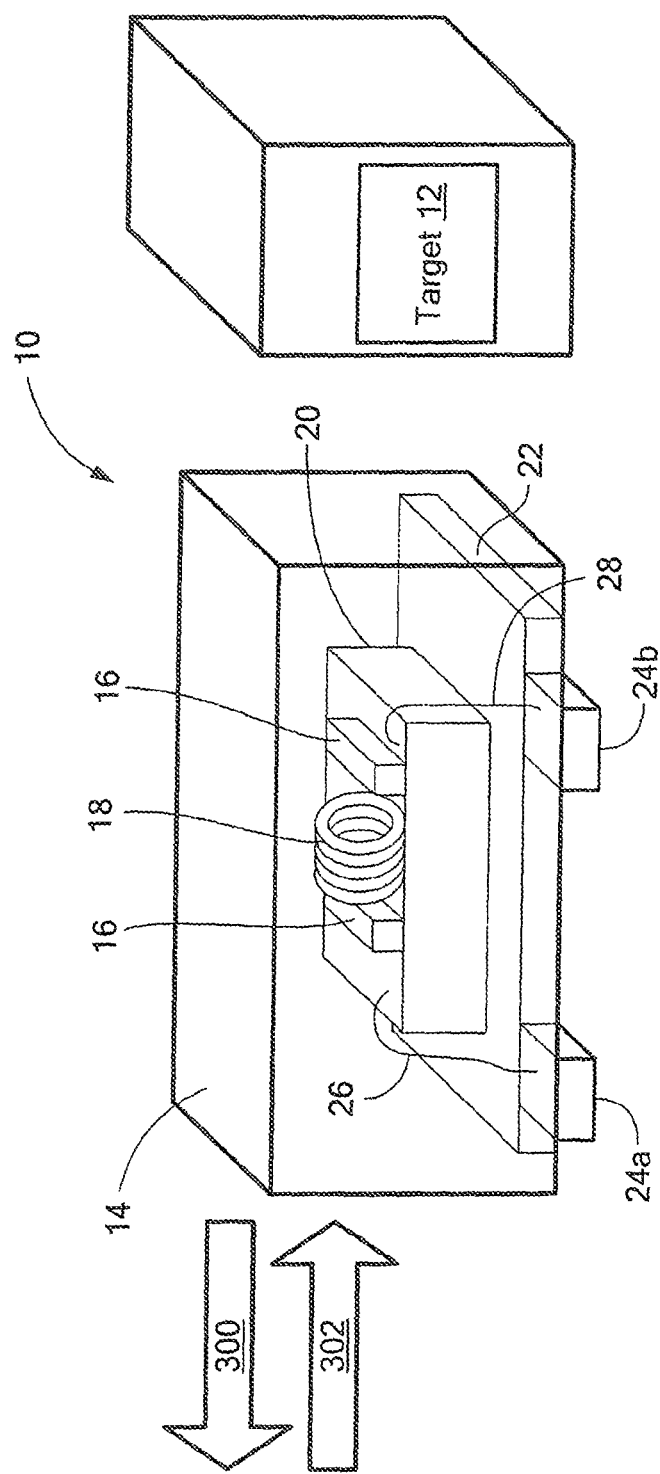
FIG. 3 is a diagram of another embodiment of a magnetic sensor having an integrated coil.

FIG. 3 shows an alternative embodiment of the sensor 10 in FIG. 1. In FIG. 3, the coil 18 is placed so that the magnetic field vector produced by coil 18 is parallel to the top surface of integrated circuit 20. In this arrangement, sensing element 16 may comprise multiple components (e.g. multiple Hall Effect elements and/or multiple GMR elements), which may be positioned on either side of coil 18. This arrangement may optimize or improve the ability of sensor 10 to detect target 12 when target 12 is located on either "side" of sensor 10. Because the magnetic field vector produced by coil 18 has a direction as shown by arrow 300 or arrow 302 (depending on the direction of current through coil 18), the magnetic field produced by target 12 may have a greater affect the magnetic field detected by sensing element 16 when target 12 is located on either side of sensor 10.

Figure 4A:
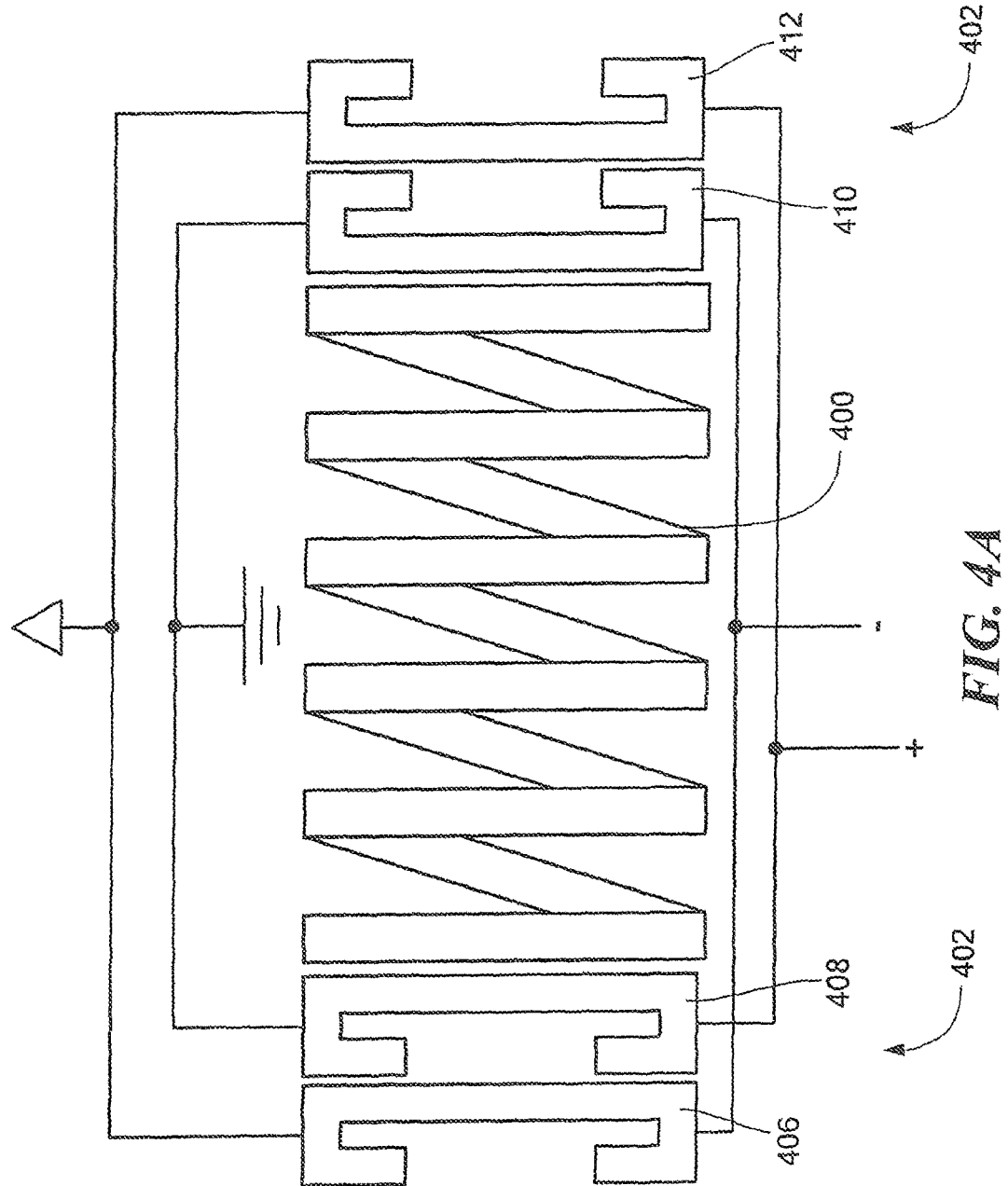
FIGS. 4A and 4B are top views of an exemplary coils.

FIG. 4A is a top view of an on-chip coil 400 and sensing element 402. In embodiments, coil 400 may be the same as or similar to coil 18 and sensing element 402 may be the same as or similar to sensing element 16. Coil 400 may comprise a toroid-shaped coil as shown in FIG. 3. Alternatively, coil 400 may comprise fabricated substantially two dimensional elements. For example, coil 400 may be a conductive layer masked and fabricated on the surface of integrated circuit 20 to create an alternating pattern of straight and diagonal metal lines on two different levels or layers of integrated circuit 20. The pattern may be formed from a single conductive layer or multiple conductive layers on integrated circuit 20, depending upon the fabrication process and design that is used. As shown in FIG. 4A, the conductive layers would be formed of multiple layers of metal, for example. An example of a single conductive layer would be a meander type of pattern where the conductor zig-zags, but does not cross over itself.

When integrated circuit 20 drives current through the printed coil, it may produce a magnetic field as described above. Similar to the coil shown in FIG. 3, coil 400 may produce a magnetic field vector tangent (parallel) to the surface of the die or substrate. Sensing element 402 may comprise GMR elements 406, 408, 410, and 410. These GMR elements may be positioned on either side of coil 400 in line with the magnetic field vector produced by coil 400 to increase sensitivity to the magnetic field.

Figure 4B:
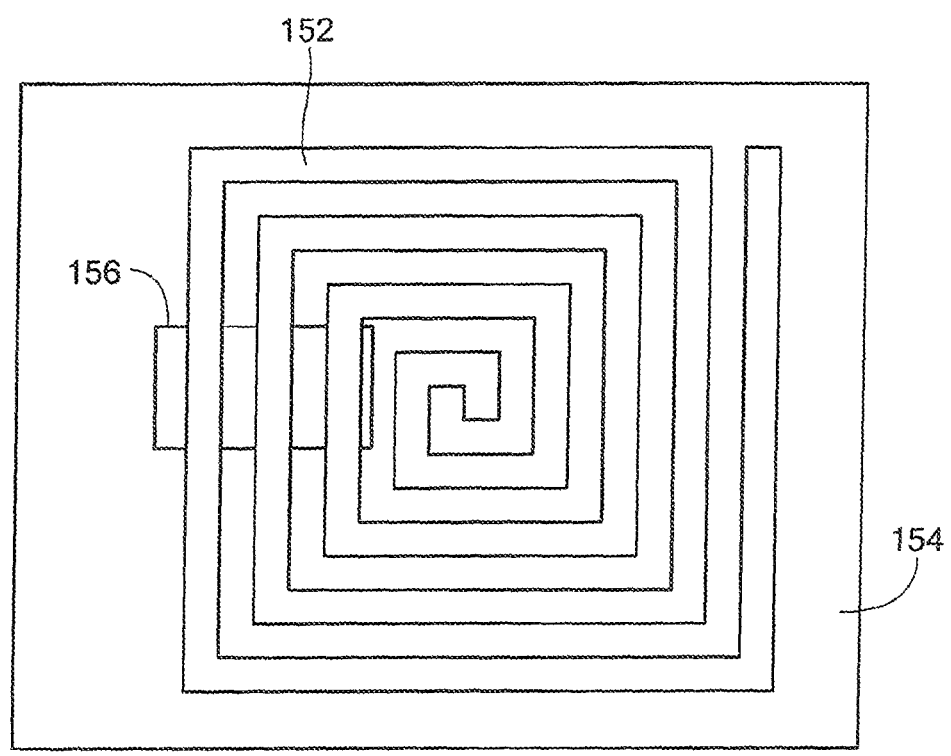

FIG. 4B shows an alternative top view layout for an exemplary magnetic field sensor having an on-chip coil 152 and a die 154 supporting a sensing element 156. The sensing element 156 is located proximate to coil 152. For simplicity, other circuitry of the magnetic field sensor are omitted.

In the illustrated embodiment of FIG. 4B, the position of the sensing element 156 is aligned with one 'side' of coil 152. That is, sensing element 156 is aligned with a portion of coil 152 in which current is flowing in the same direction with respect to one side of the die. Other arrangements of coil relative to sensing element position are possible. For example, the sensing element can be generally centered with respect to the coil. In such an embodiment, a sensing element comprising a planar Hall element may be preferred. Also, and again referring to the example embodiment shown in FIG. 4B, coil 152 is shown as being disposed above sensing element 156. It will be understood, however, that coil 152 could instead be disposed beneath the sensing element 156. In other embodiments coil 152 may have layers or conductors above and below sensing elements 156. With the latter arrangement, the coil can be fabricated with a standard IC process and then integrated with sensing element 156 in a separate process. The embodiment shown would be advantageous for a sensor sensitive in the plane of the die such as a vertical Hall element or a GMR, AMR, spin-valve, or TMR element.

Insulation layers may be placed between the coil and sensor material and/or die substrate as required by sensor and substrate material selection so as not to short circuit the materials and coil.

The particular size and geometry of the coil can vary to meet the needs of a particular application. The coil can be formed so that the turns have any practical shape, such as a square or rectangle (as illustrated in the top view of FIGS. 4A and 4B), or other shapes such as circle, oval, etc., or multiple layers.

In exemplary "on-chip" coil embodiments, the coil is formed using conventional deposition and or etching processes, or patterning and electroplating processes well known to one of ordinary skill in the art. In general, spacing from the coil to the sensing element can vary, in part as a result of voltage isolation requirements and magnetic coupling required, where magnetic coupling is the magnetic field produced by the coil per mA or other unit of current flowing in the coil. In general a higher magnetic coupling level uses less power for a given magnetic field level. It is also understood that insulation layers may be placed between the coils and the sensors and/or other die material to prevent shorting of the coil to other electrical layers in the device.

In FIG. 4B, the coil is shown as having a planar spiral geometry. The vias and connections are omitted in the figure (for clarity) but would be apparent to one of ordinary skill in the art. It is understood that multiple metal layers can be used as well as other geometries of metal. Other coil geometries including but not limited to meander coils and solenoids may be used. For example, a cylindrical coil having coil turns of substantially uniform diameter (i.e., a solenoid type coil) may be used. The coil arrangement can include a magnetic flux concentrator, which can be made of a soft magnetic material, to improve the magnetic flux generated by the coil. For example, a soft ferromagnetic core may be provided inside a solenoid type coil to concentrate the magnetic field generated by the coil.

In a cylindrical coil the direction of the magnetic field lines will be parallel to the length of the coil (that is, the longitudinal path of the coil). In a planar spiral coil design the direction of the field lines at the center of the coil will be substantially perpendicular to the plane of the coil but will be substantially parallel to the die surface under the turns of the coil. Consideration may be given to the direction of the field generated by the coil at various locations in choosing the appropriate position and type of the sensing element.

It will be appreciated that the size of an "on-chip" coil as depicted in FIGS. 4A and 4B is likely to be much smaller than coils located elsewhere in a sensor, sensor assembly or application. Because magnetic fields generated by the relatively smaller "on-chip" coils may not be particularly strong, high sensitivity elements such as GMR may be more suitable for an on-chip coil design than less sensitive sensing types of elements such as Hall.

Additional details or alternative techniques for providing a conductive coil on a sensor die may be had with reference to U.S. patent application Ser. No. 13/468,478, filed May 10, 2012 and entitled "Methods and Apparatus for Magnetic Sensor Having Integrated Coil," as well as U.S. Patent Publication No. 2010/00211347, U.S. Pat. Nos. 8,030,918, and 8,063,634, each of which is assigned to the Assignee of the subject application and incorporated herein by reference in its entirety.

Figure 5:
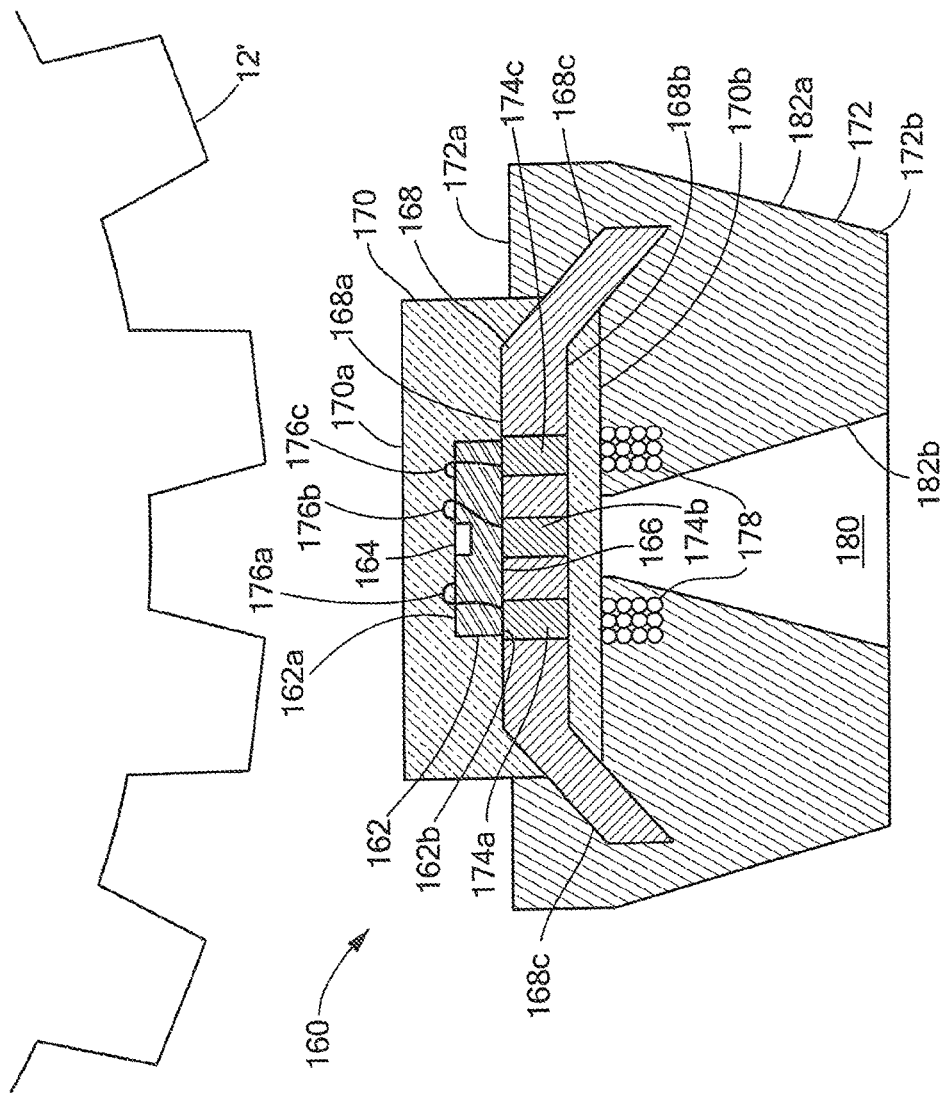
FIG. 5 is a diagram of an embodiment of a magnetic sensor having an integrated coil and a target.

Referring to FIG. 5, another embodiment of a magnetic field sensor 160 including a semiconductor die 162 having a first, active surface 162a in which a magnetic field sensing element or sensing element 164 is formed and a second, opposing surface 162b attached to a die attach area 166 on a first surface 168a of a lead frame 168, a first mold portion comprising a non-conductive mold material 170 enclosing the die and at least a portion of the lead frame, and a second mold portion 172 secured to the non-conductive mold material. The second mold portion 172, which can be a non-conductive material or a ferromagnetic material, is shown as but not required to be tapered from a first end 172a proximate to the lead frame 168 to a second end 172b distal from the lead frame.

Sensing element 164 in this and other embodiments may be the same as or similar to sensing element 16.

It will be appreciated by those of ordinary skill in the art that while the active surface 162a of the semiconductor die 162 is described herein as the surface "in" which the magnetic field sensing element is disposed or formed as is the case with certain types of magnetic field elements (e.g., Hall plate), the element may be disposed "over" or "on" the active semiconductor surface (e.g., magnetoresistance elements). For simplicity of explanation however, while the embodiments described herein may utilize any suitable type of magnetic field sensing elements, such elements will be described generally herein as being formed or disposed "in" the active semiconductor surface.

In use, the magnetic field sensor 160 like the other sensor embodiments described herein may be positioned in proximity to a ferromagnetic target, such as the illustrated gear 12', such that the magnetic field sensing element 164 is adjacent to the article 12' and is thereby exposed to a magnetic field altered by movement of the article. The magnetic field sensing element 164 generates a magnetic field signal proportional to the magnetic field.

The magnetic field sensor 160 generally includes additional circuitry formed in the active surface 162a of the die 162 for processing the magnetic field signal provided by the sensing element 164. The lead frame 168 includes leads 174a-174c for coupling the circuitry to system components (not shown), such as a power source or microcontroller. Electrical connection between the leads 174a-174c and the semiconductor die 162 can be provided with wire bonds 176a-176c, respectively as shown. While the sensor 160 is shown to include three leads 174a-174c, it will be appreciated by those of ordinary skill in the art that various numbers of leads are possible. Other techniques for electrically coupling the lead frame leads to the sensor components include solder bumps or balls, or pillar bumps. The sensor 160 may be provided in the form of a two to six pin Single In-Line (SIP) package, or some other number of pins as appropriate.

The first mold portion 170 is comprised of a non-conductive material so as to electrically isolate and mechanically protect the die 162 and the enclosed portion of the lead frame 168. Suitable materials for the non-conductive mold material 170 include thermoset and thermoplastic mold compounds and other commercially available IC mold compounds.

The non-conductive mold material of the first mold portion 170 is applied to the lead frame/die subassembly during a molding process to enclose the die 162 and a portion of the lead frame 168. The non-conductive first mold portion 170 has a first surface 170a and a second, opposing surface 170b. The shape and dimensions of the non-conductive first mold portion are selected to suit a particular IC package.

The second mold portion 172 may be the same non-conductive mold compound used to form the first mold portion 170. In some embodiments the second mold portion 172 is a different non-conductive mold compound or other moldable material than the material used for the first mold portion 170.

In some embodiments, the second mold portion 172 is comprised of a soft ferromagnetic material to form a concentrator. As will be apparent to those of ordinary skill in the art, various materials are suitable for providing the ferromagnetic mold material 172 in the form of a soft ferromagnetic material. In some embodiments, it may be desirable for the soft ferromagnetic mold material to have a relatively low coercivity and high permeability. Suitable soft ferromagnetic materials include, but are not limited to permalloy, NiCo alloys, NiFe alloys, steel, nickel, and soft magnetic ferrites.

The second mold portion 172 can be secured to the first mold portion 170 during a step or steps of a molding process, or using an adhesive, such as a thermoset adhesive (e.g., a two part epoxy).

In some embodiments, a portion of the first mold portion 170 that contacts the second mold portion 172 and/or the portion of its mold material that contacts the non-conductive mold material has a securing mechanism in order to improve the adhesion between the two materials and to prevent or reduce lateral slippage or shear between the materials. As one example, the lead frame 168 has extensions 168c (or "barbs") which extend beyond the non-conductive mold material and are enclosed by the mold material of the second mold portion 172, as shown. Such lead frame extensions additionally enhance the adhesion of the second mold portion/material to the lead frame itself. In such embodiments utilizing lead frame portions as a securing mechanism such that the mold material of the second mold portion 172 contacts such lead frame portions, it will be appreciated that the second mold portion 172 should be non-conductive or have a sufficiently low conductivity to prevent the leads from electrically shorting resulting in the device not operating as intended. Alternative forms of securing mechanisms can be used.

Still referring to FIG. 5, the sensor 160 also includes a coil, indicated in this figure by reference numeral 178. In embodiments, coil 178 is a package level coil, i.e. a coil incorporated into package mold portion 172. Coil 178 may perform the same or similar function to coil 18. Coil 178 is positioned relative to sensing element 164 to provide a back bias magnetic field, which can be used to detect the target's profile as it passes the sensor. To this end, the coil 178 is positioned adjacent to the second surface 170b of the non-conductive mold material 170 so that the sensing element 164 is closer to the target 12' than the coil 178, as shown. It will be appreciated that it may be desirable in certain applications to rotate sensor 160 by 180° so that the coil 178 is closer to the target than the sensing element or to rotate the sensor by 90° so that the major face of the sensing element is orthogonal to the target, thereby achieving a different type of magnetically sensitive sensor, as may be desirable when the sensing element is a magnetoresistance element, for example, which has a different axis of sensing element sensitivity than a planar Hall element. It may also be desirable in an embodiment to rotate coil 178 such that its central axis is parallel to the surface of the die 162 for certain sensor configurations and sensing element combinations.

Various techniques and materials can be used to form the coil 178. For example, coil 178 can be formed from copper wire of various sizes and with various automated processes so as to provide an insulator between coil windings. The coil material selection, wire gauge selection, number of turns, and other design choices can be readily varied to suit a particular application so as to produce a magnetic field of a desired strength. The coil 178 may be formed so that each turn is in the general shape of, or approximately the shape of, a circle, rectangle, or other general shapes such as an oval, as desirable to suit a particular application and packaging arrangement.

Coil 178 may be secured to the second surface 170b of the non-conductive mold material 170 by various means. As one example, an adhesive, such as an epoxy, may be used to secure the coil in place. Once secured in place, the mold material 172 may be formed by a suitable molding process, such as by injection molding for example.

A mold cavity used to define the second mold portion 172 may include a mandrel so that the second mold portion forms a ring-shaped structure having a central aperture 180, here extending from the second surface 170b of the non-conductive mold material to a second end 172b of the second mold portion. The mold material 172 may form a conventional O-shaped ring structure or a D-shaped structure. Alternatively, the mold material 172 may form only a partial ring-like structure, as may be described as a "C" or "U" shaped structure. More generally, the mold material 172 comprises a non-contiguous central region such that the central region is not formed integrally with its outer region. Such central region may be an open area, such as in the case of aperture 180 in FIG. 8, or may contain a mold material, for example, a ferromagnetic mold material. A third mold material may be formed by an additional molding step or other suitable fabrication technique, including but not limited to "potting" or another molding step, so as to secure that third mold material to the second mold portion 172. The third mold material may be comprised of a hard ferromagnetic material, a soft ferromagnetic material, or a non-ferromagnetic mold compound.

The second mold portion 172 is tapered from its first end 172a (or a location close to its first end) to its second end 172b as is apparent from the side view of FIG. 5. In particular, the second mold portion has a first taper to its outer circumferential surface 182a and a second taper to its inner central aperture surface 182b. The purpose of the taper is to facilitate removal of the sensor 160 from the mold cavity. The angle of the taper of the surfaces 182a, 182b may be the same or similar to each other and generally, the angle of the taper of the surfaces 182a, 182b is less than approximately 15 to 20 degrees. In some embodiments, the angle of taper is on the order of 2-7 degrees. In some embodiments the taper 182b may have more than a single slope.

The sensor can also be arranged in a lead on chip configuration with the lead frame positioned above the die. An adhesive may be used to secure the lead frame to the active surface of the die.

Figure 6:
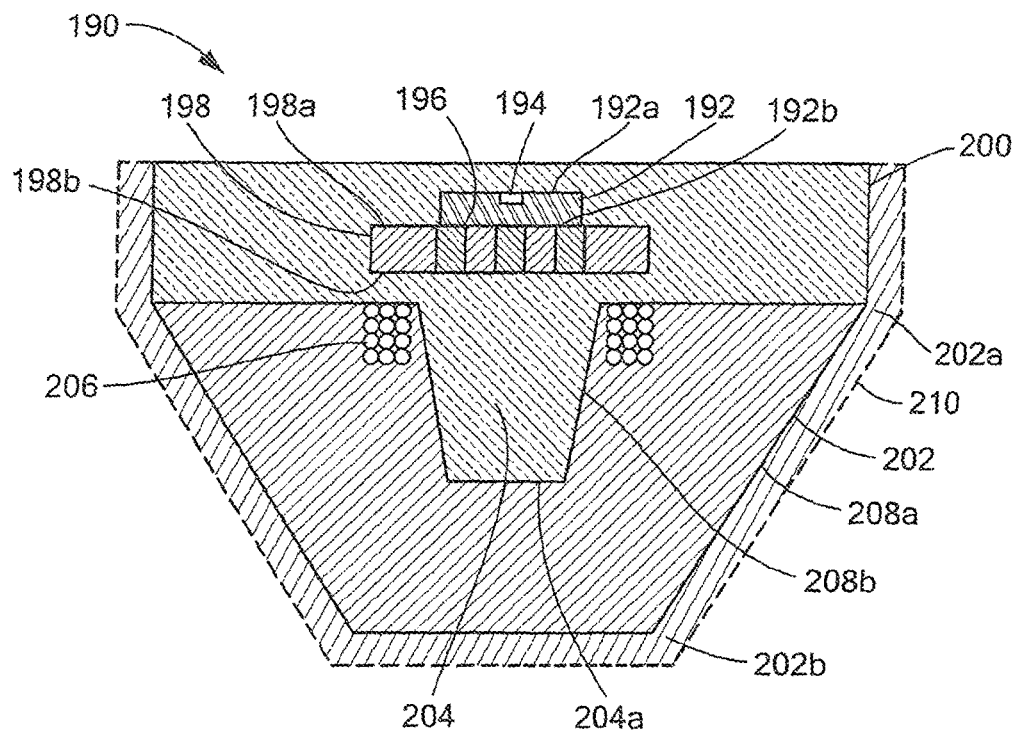
FIG. 6 is a diagram of an embodiment of a magnetic sensor having an integrated coil.

Referring to FIG. 6, an alternative magnetic field sensor 190 includes a semiconductor die 192 having a first active surface 192a in which a magnetic field sensing element 194 is disposed and a second, opposing surface 192b attached to a die attach area 196 on a first surface 198a of a lead frame 198, a first mold portion or non-conductive mold material 200 enclosing the die and at least a portion of the lead frame, and a second mold portion or mold material 202 secured to a portion of the non-conductive mold material. A securing mechanism, or other suitable mechanisms, may be provided to enhance the adhesion between the first and second mold materials. In embodiments, sensor 190 may be the same as or similar to sensor 10.

The non-conductive mold material 200 has a protrusion 204 extending away from a second surface 198b of the lead frame 198 as shown. Protrusion 204 prevents there being a void in the bottom surface of sensor 190 (adjacent to the second end 202b of the mold material), since the presence of a void may make overmolding more difficult. It will be appreciated by those of ordinary skill in the art that the protrusion may extend all or only part of the way to the second end 202b of the second mold material 202. In the illustrated embodiment of FIG. 6, protrusion 204 terminates before the second end 202b of the second mold material 202. Thus, distal end 204a of the protrusion 204 is covered with the second mold material 202, as shown. It will also be appreciated that the protrusion 204, which is shown extending beyond (e.g. below) coil 206, may extend to a position that is not below coil 206. If protrusion 204 extends to a position that is not below coil 206, the second mold material 202 would generally enclose the protrusion 204 and the coil 206.

Sensor 190 includes a coil 206 that may be the same as or similar to the coil 18 of FIG. 1. Here, coil 206 is positioned concentrically with respect to the protrusion 204 of the non-conductive mold material 200, although it will be appreciated that concentric positioning is not required. It will be appreciated that the taper to protrusion 204 may be eliminated or altered as suitable for a particular application. In some applications the protrusion may be useful as an aligning feature for coil 206 during assembly or manufacturing. Here again, coil 206 may be secured to the mold material 200 by an adhesive. Alternatively however, coil 206 may be sized and shaped to provide an interference fit with respect to the protrusion 204 such that adhesive is not necessary and coil 206 may be sufficiently held in place relative to the mold material 200 by the interference fit when the subassembly, including the mold material 200, lead frame 198 and die 192, are placed into the mold cavity for formation of the mold material 202.

While sensor 190 is shown to have a protrusion 204 extending only partially through mold material 202 to terminate before the second end 202b of the second mold material 202, it will be appreciated that a similar sensor including a coil that may be (although is not required to be) concentrically disposed with respect to a protrusion of the non-conductive mold material can be provided with a protrusion of the type which extends to the second end 202b of second mold material 202 or the protrusion 204 may extend beyond the second end 202b of the second mold material 202.

The second mold material 202 is tapered from a first end 202a proximate to the lead frame 198 to a second end 202b distal from the lead frame. The second mold material 202 is tapered along both its outer circumferential surface 208a and its inner surface 208b from its first end 202a to its second end 202b. Here again, the angle of taper of the surface 208a may be on the order of less than 15-20 degrees. The angle of the taper of the inner surface 208b may be the same as or similar to the angle of the taper of the outer surface 208a.

The second mold material 202 has a non-contiguous central region, here in the form of a central aperture defined by the inner surface 208b. This non-contiguous central region of mold material 202 may take various shapes, so as to form an O-shaped, D-shaped, C-shaped, or U-shaped structure as examples.

The second mold material can be provided in the form of a non-conductive material or ferromagnetic material such as a soft ferromagnetic material or hard ferromagnetic material. For example, in embodiments in which the material is a soft ferromagnetic material, the magnetic field generated by the coil can be focused or otherwise concentrated as desired by the soft ferromagnetic mold material. Alternatively, in embodiments in which the material is a hard ferromagnetic material, the magnetic field provided by the coil can be used to modulate the magnetic field provided by the hard ferromagnetic material, in order to thereby reduce the peak current otherwise required to provide the same magnetic field strength with just the coil (i.e., if the hard ferromagnetic mold material were not present). Since the back bias functionality is provided by the coil, the second mold portion/material may be eliminated entirely (as is shown in FIG. 10) in which case the non-conductive mold material with the coil attached to its surface can be packaged to provide the resulting sensor IC. Such an arrangement can be provided in a package of the type described in a U.S. Pat. No. 6,265,865 or a U.S. Pat. No. 5,581,179, each of which is assigned to the Assignee of the subject application and incorporated herein by reference in its entirety.

In applications including the second mold portion/material, such mold material may be tapered from a first end proximate to the lead frame to a second end distal from the lead frame (or for some portion thereof) and the sensor may, optionally, include a third mold material in the form of an overmold in order to protect and electrically insulate the device.

Sensor 190 may, optionally, include a third mold material 210 in the form of an overmold in order to protect and electrically insulate the device. The third mold material 210 may be applied during a third molding step/process or alternatively by any suitable fabrication method. Overmold 210 is considered optional because its purpose is to provide electrical insulation. In embodiments in which ferromagnetic mold material 202 provides sufficient insulation (e.g., provides more than approximately 1 mega-Ohm of resistance in certain applications), overmold 210 may be eliminated. It will be appreciated that overmold 210 may be provided for the sensor of FIG. 1, 3, 4, 5 and other embodiments. Suitable materials for providing overmold material 210 include, but are not limited to standard die encapsulation mold compounds such as PPS, nylon, SUMIKON® EME of Sumitomo Bakelite Co., Ltd., or Hysol® mold compounds of Henkel AG & Co. KGaA.

Figure 7:
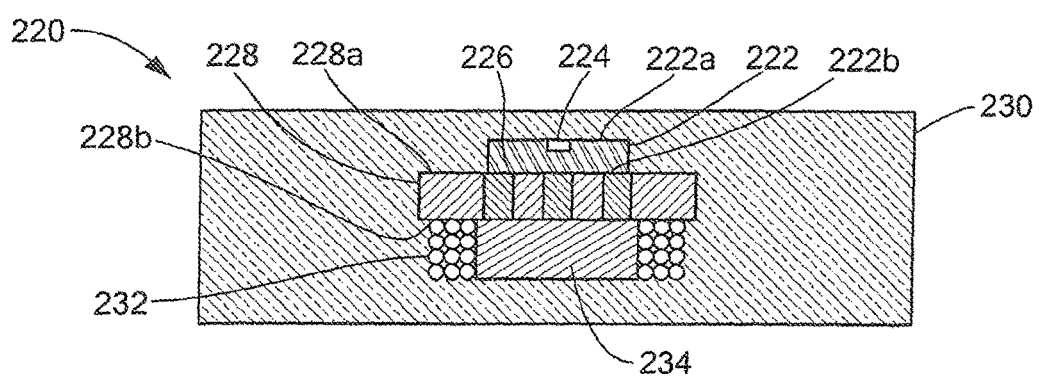
FIG. 7 is a diagram of an embodiment of a magnetic sensor having an integrated coil.

Referring to FIG. 7, an alternative magnetic field sensor 220 includes a semiconductor die 222 having a first active surface 222a in which a magnetic field sensing element 224 is disposed and a second, opposing surface 222b attached to a die attach area 226 on a first surface 228a of a lead frame 228 and a non-conductive mold material 230 enclosing the die and at least a portion of the lead frame. In an embodiment, sensor 220 may be the same as or similar to sensor 10.

Sensor 220 includes a coil 232 secured to, and more particularly, enclosed by, the non-conductive mold material 230. The wire of coil 232 may be wound around a mandrel or bobbin 234, as shown. In one illustrative embodiment, mandrel 234 may be comprised of a soft ferromagnetic material or a plastic and remain part of the final device. In other embodiments, mandrel 234 is used during coil winding but then not made a part of the final package. Mandrel 234 and coil 232 may be secured to the surface 228b of lead frame 228 that is opposite the die 222 with an adhesive or other securing mechanism such that coil 232 is secured to the lead frame 228 when the subassembly is placed in a mold cavity and the non-conductive mold material 230 is formed.

Additional details or alternative techniques for providing a package with one or multiple mold materials may be had with reference to U.S. patent application Ser. No. 13/748,999, filed Jan. 24, 2013 and entitled "Magnetic Field Sensor Integrated Circuit with Integral Ferromagnetic Material," which is assigned to the Assignee of the subject application and incorporated herein by reference in its entirety. Other examples of securing mechanisms include the use of an adhesive material and/or various other features designed to provide interference and/or an interlocking mechanism between the mold materials.

The signal may be provided to the coil through extra pins, allowing an external connection to the coil. The signal may be an AC signal, a ramped signal, a pulsed signal, or any other type of changing (e.g. non-DC) signal that, when applied to the coil, can produce a changing magnetic field. Alternatively, the signal could be provided through connections to the die. For example, a wire coupled to a coil terminal could be soldered to the die or connected to the die via wire bonds. In an alternative embodiment, a portion of the lead frame could be used to connect to the coil wire and to the die (e.g., via a wire bond). These connection areas of the lead frame could be unconnected to the remainder of the lead frame after molding and trimming. Any other suitable connecting means could be used.

Figure 8:
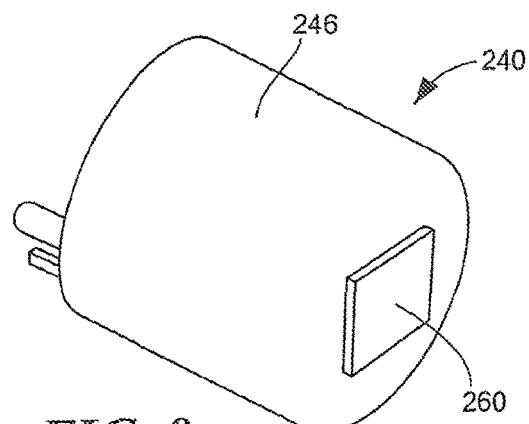
FIG. 8 is a diagram of a magnetic sensor assembly.
Figure 9:
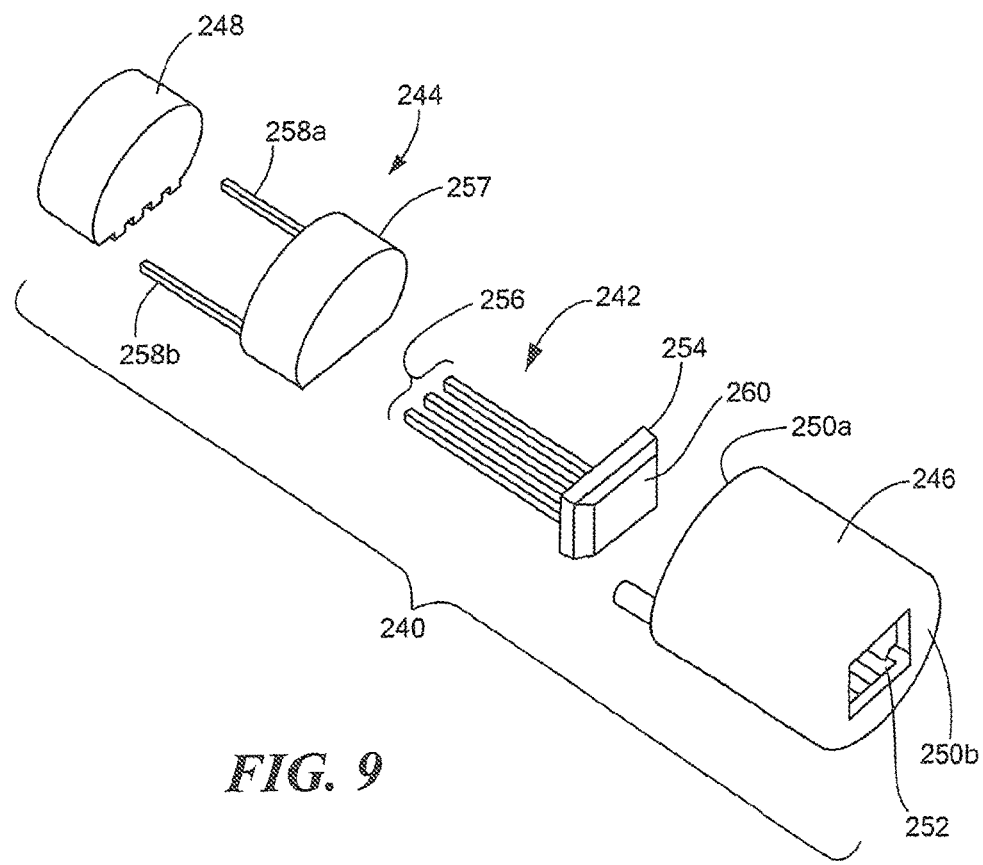
FIG. 9 is a break-out diagram of a magnetic sensor assembly.

FIGS. 8-9 illustrate yet another type of packaging for a magnetic field sensor with a coil. Referring to FIGS. 8 and 9, a magnetic field sensor assembly 240 includes a packaged magnetic field sensor IC 242, a coil unit 244, and a housing having a case (or housing shell) 246 and an end cap 248. Case 246 has a first end 250a with an opening (not shown) and a second end 250b that includes a window 252. When each of these elements is serially placed through the opening 250a of case 246 (in the order of sensor IC 242, then coil unit 244 followed by the end cap 248, as shown in the exploded view of FIG. 9), the "fully assembled" magnetic field sensor assembly 240 takes on the form shown in the configuration shown in FIG. 8. Although the housing is shown as a two-piece housing having a generally cylindrical shape, other types of housings could be used as well.

The packaged magnetic field sensor IC 242 is shown to include a first package portion 254 corresponding to a magnetic field sensor chip within a protective package body and a second package portion, in the form of conductive leads 256. There may be three conductive leads 256, with a lead to correspond to the power and ground connections and a lead for the output signal (as shown in the embodiments of FIGS. 3 and 6, for a "three-wire" device), or some other number of leads. Coil unit 244 may include a coil body portion 257 containing a coil (which can be, e.g., a spiral coil, a solenoid type coil, solenoid type coil with a soft ferromagnetic core, or other type of coil configuration) and conductive leads 258a and 258b. Materials for the entire coil body portion 257 (exclusive of the internal coil) may include plastic (or other mold compound) or non-ferromagnetic material.

Alternatively, for a coil unit design that integrates a magnetic flux concentrator or guide, the top of coil body portion 257 (i.e., the part between the coil and the sensing element of the sensor 242 IC) could be made of plastic (or other mold compound) or non-ferromagnetic material, and the sides and bottom of coil body portion 257 could be made of a soft ferromagnetic material to help reduce the reluctance path, i.e., guide the magnetic flux more efficiently.

One of the leads, e.g., lead 258a, is a signal input for connecting to the signal source (e.g., coil input line 26, shown in FIG. 1). As described above, the signal source may be a changing signal (i.e. a non-DC signal) that can produce a changing magnetic field when applied to the coil. The other lead, e.g., lead 258b, is a ground terminal for connecting to a reference potential (e.g. ground). The coil of coil unit 244 may be driven in electrical isolation from the sensor IC 242 with no common node. If, however, the sensor IC ground and the coil unit ground are to be tied together, then the assembly 240 could be designed to have one less pin/lead for external connections. In the assembly 240, the leads 256 of the packaged sensor IC and leads 258 of the coil unit 244 extend outwardly from the opening in the first end 250a of the case 246. The first package portion 254 is positioned in the case 246 part way through the window 252 so that a first body face 260 extends outwardly from second end 250b of the case 246. When the sensor assembly 240 is mounted in an application, the first body face 260 will be positioned in proximity to the target's profile.

The illustrative housing of FIGS. 8-9 can be constructed according to techniques like those described in the above-referenced U.S. Pat. No. 5,581,179, or other suitable techniques. The case 246 can be formed of a polymeric insulating material, as described in the aforementioned patent, or, alternatively, a soft ferromagnetic material. In other embodiments, a separate magnetic flux concentrator may be included in the assembly.

Figure 10A:
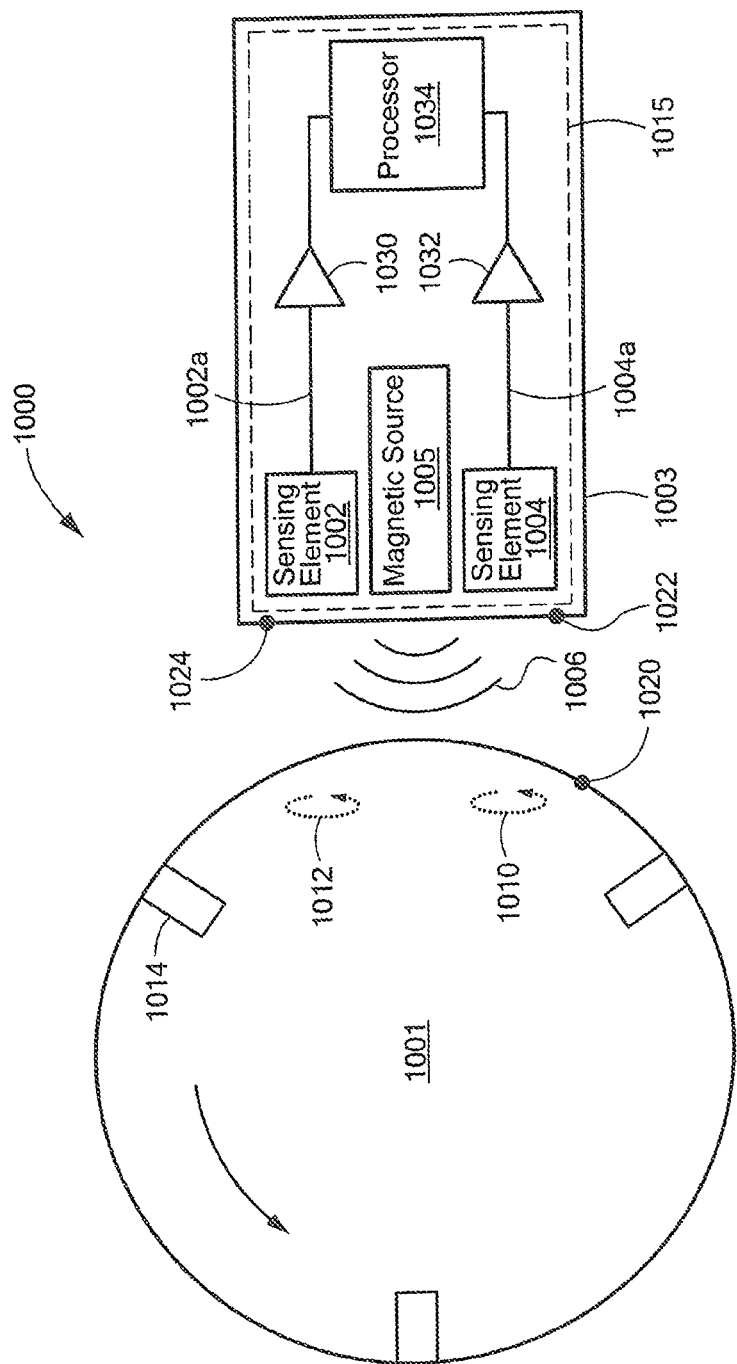
FIG. 10A and FIG. 10B are diagrams of magnetic sensors and targets.
Figure 10B:
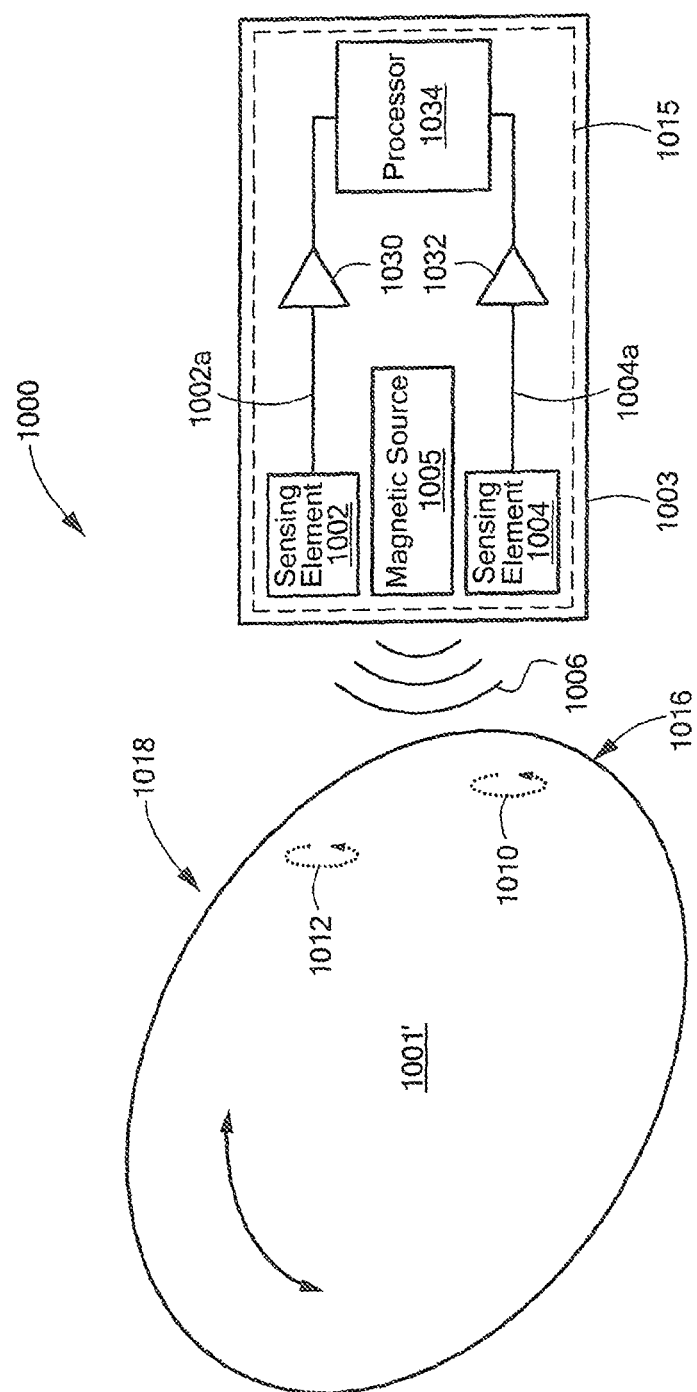

FIG. 10A and FIG. 10B illustrate examples of a magnetic sensor system 1000 for detecting a non-ferromagnetic target 1001. As shown in FIG. 10A, sensor system 1000 includes a magnetic field sensor 1003 having one or more magnetic field sensing elements 1002 and 1004. Sensor 1003 may include a sensor integrated circuit or die 1015 and one or more magnetic sources (e.g. coils or magnets, such as a back-bias magnet) 1005 capable of producing magnetic field 1006. Although shown as having two magnetic field sensing elements 1002 and 1004, sensor 1003 may contain fewer or more than two sensing elements. Although shown as having a single magnetic source, sensor 1003 may include multiple magnetic sources. One skilled in the art will recognize that, if sensor 1003 has more than one magnetic source, the magnetic fields produced by those sources may be viewed as a single, combined magnetic field 1006 produced by multiple discrete sources. It is also noted that the orientation of the magnetic source to the sensing element or sensing elements shown in FIGS. 10A and B is schematic in nature and may be modified in various embodiments. For example, sensor 1003 (and/or die 1015) may be positioned between a magnetic source 1005 and a target 1001. In other embodiments the magnetic source or sources and sensing element or elements have different positions relative to the target.

Sensing elements 1002 and 1004 may be the same as or similar to any or all of the sensors described above with respect to the preceding FIGS. 1-9. In other embodiments sensing elements 1002 and 1004 could be separate magnetic field sensors joined by some common circuitry or with the output of one sensor used as an electrical input to another sensor if the two sensors with their sensing elements were in separate packages. As described above, sensing elements 1002 and 1004 may include a magnetic source 1005 (e.g. a coil and/or magnet) to produce a magnetic field 1006. Alternatively, magnetic source 1005 may be mounted separately from die 1015. In such an embodiment, source 1005 may be positioned relative to target 1001 so that a magnetic field 1006 intersects the body of target 1001. Although magnetic source 1005 is shown in FIGS. 10A and 10B as part of die 1015, this is not a requirement. In various embodiments, magnetic source 1005 may be separate from die 1015, part of die 1015, mounted or placed adjacent to or on die 1015, etc. For example, in various embodiments, magnetic source 1005 may be arranged in any configuration or arrangement that allows magnetic source 1005 to produce a magnetic field 1006 that can be detected by sensing elements 1002 and/or 1004. Examples of such configurations and arrangements are described above in relation to FIGS. 1-9.

As described above, magnetic field 1006 or may be a static magnetic field produced by a permanent magnet (e.g. a hard ferromagnetic material) or an electromagnet with a DC or other slowly changing current to produce a magnetic field.

Although shown having two sensing elements 1002 and 1004, system 1000 may include only a single sensing element, or may include more than two sensing elements. As will be described below, one or more sensing element(s) can be used to detect proximity, presence, speed, direction, and other properties of target 1001.

In an embodiment, target 1001 is a non-ferromagnetic target. Target 1001 may comprise a conductive material such as copper, aluminum, titanium, etc., and may have a size and thickness that allow eddy currents to form within, on, or near the surface of target 1001.

In operation, magnetic source 1005 produces magnetic field 1006 and sensing elements 1002 and 1004 react to or sense magnetic field 1006. In an embodiment, sensing elements 1002 and 1004 generate signals 1002*a* and 1004*a*, respectively. Amplifiers 1030 and 1032 receive these signals, amplify them, and supply them to processor 1034. Processor 1034 then processes the signals to determine presence, speed, direction, position, or other properties of target 1001. In other embodiments other variations of circuitry could be used to sense the target.

Through operation of Faraday's law of induction, since the body of target 1001 is conductive (and/or paramagnetic), magnetic field 1006 induces an eddy current (e.g. eddy current 1010 and/or eddy current 1012) on or near the surface of target 1001. In the case where magnetic fields 1006 is a changing magnetic field, changes in the magnetic field will induce the eddy currents in target 1001. In the case where magnetic field 1006 is a static magnetic field, motion of the conductive target through the magnetic field, cause eddy currents 1010 and 1012 to form within target 1001 or 1001'. Irregular features or shapes of the target can influence the presence or magnitude of the induced eddy currents.

Multiple eddy currents 1010 and 1012 are shown for ease of illustration. One skilled in the art will recognize that magnetic field 1006 may induce a single eddy current or multiple eddy currents in target 1001, which may be added or combined together to form a combined eddy current within target 1001. In certain embodiments, magnetic source 1005 may be configured to produce a shaped magnetic field 1006. In other words, magnetic source 1005 may produce multiple magnetic fields that add together in various patterns so that the resulting, combined magnetic field has local areas that are relatively strong and local areas that are relatively weak. In such embodiments, magnetic source 1005 may comprise multiple coils, magnets, or other magnetic sources. By shaping the magnetic field 1006, magnetic source 1005 can control the location, direction, and strength of the eddy currents 1010 and 1012 induced in target 1001.

The eddy currents 1010 and 1012 formed within target 1001 create their own, secondary magnetic fields, which oppose changes in magnetic field 1006 in the target 1001. These magnetic field changes can be due, for example, to magnetic source 1005 changing the strength or shape of magnetic field 1006 over time. In other embodiments, if magnetic field 1006 is a static (e.g. non-changing, or slowly-changing) magnetic field, the motion (e.g. rotation) of target 1001 through magnetic field 1006 may cause target 1001 to produce eddy currents which result in changes to the magnetic field 1006. The magnetic fields caused by eddy currents 1010 and 1012 will tend to oppose the changes in magnetic field 1006, and may increase or reduce the amount of magnetic flux flowing through the magnetic sensing elements 1002 and 1004. Thus, eddy currents 1010 and 1012 will tend to increase or reduce the amplitude of the signals produced by the magnetic field sensing elements 1002 and 1004. In contrast, if target 1001 were not present, no eddy currents or opposing magnetic field would be induced, and thus the amplitude of the signals produced by the magnetic field sensing elements would not be increased or reduced. Accordingly, system 1000 can detect the presence of target 1001 by detecting a change in amplitude of the signals produced by sensing elements 1002 and 1004, and due to the presence of eddy currents in the target.

In the case where magnetic field 1006 is a static magnetic field, motion of the target through the magnetic field causes changes to eddy currents 1010 and 1012. As shown in FIG. 10A, a point 1020 on the surface of target 1001 may have negligible magnetic field when it is relatively distant from magnetic source 1005. As point 1020 approaches a point 1022 on sensor 1003, it will be exposed to an increasing magnitude of magnetic field 1006, and thereby create eddy current 1010 to oppose that change. Similarly, as point 1020 passes point 1024 on sensor 1003, it will see a decrease in the magnetic field from magnetic source 1005, thus creating an eddy current 1012 to oppose this change.

Given the direction of target rotation shown by arrow 1026, eddy current 1010 will reduce the field sensed by magnetic field sensing element 1004, and eddy current 1012 will increase the field sensed by magnetic field sensing element 1002. If the direction of rotation is opposite, eddy currents 1012 and 1010 will be of opposite magnitude, i.e. eddy current 1010 will increase the field sensed by magnetic field sensing element 1004 and eddy current 1012 will decrease the field sensed by magnetic field sensing element 1002. Thus, the amplitude of the signal produced by magnetic field sensing elements 1002 and 1004 may depend the direction of target rotation. Accordingly, system 1000 can detect the direction of target 1001 rotation by detecting a change in the signals produced by sensing elements 1002 and 1004, spatially located in system 1000.

Magnetic field sensing elements 1002 and 1004 may be spatially arranged so that there is a physical distance between them. Spacing the sensing elements apart in this way can allow each sensing element 1002 and 1004 to detect magnetic fields produced by eddy current in a different, localized area of target 1001. For example, as shown, sensing element 1002 is closer to eddy current 1012 and sensing element 1004 is closer to eddy current 1010. Thus, the magnetic field sensed by sensing element 1002 will be more greatly affected by eddy current 1012 and the magnetic field sensed by sensing element 1004 will be more greatly affected by eddy current 1010.

Target 1001 may also have irregular features, such as feature 1014. Feature 1014 may be a valley, gap, recess, a non-conductive region, a less conductive region, or any type of region that changes the eddy currents 1010 and 1012 induced by magnetic fields 1006 and 1008. In another embodiment, the feature 1014 could be a tooth, bump, or protrusion of the target. In another embodiments combinations of gaps and protrusions would be possible, for example, but not limited to approximately three different radial distances from the center of rotation, i.e. a valley, a nominal radius, and a tooth. Thus, when feature 1014 is adjacent to magnetic field 1006 or 1008, the eddy current induced in target 1001 may be different from the eddy current induced when feature 1014 is not adjacent to magnetic field 1006 or 1008. For example, if feature 1014 is a gap or a non-conductive region, there may be no eddy current induced within region 1014 and no opposing magnetic field. Alternatively, an eddy current may be induced in feature 1014, but the eddy current may have a different strength or magnitude than eddy current 1012 or 1010 that are induced in the main body of target 1001.

The sensor 1003 and sensing elements 1002 or 1004 may detect a change in the magnetic field due to the presence of feature 1014 and produce a signal indicating that feature 1014 has been detected. If the target is rotating at a particular speed, peaks or valleys may appear on signals 1002*a* and 1004a as feature 1014 passes by sensing element 1002 and 1004. Processor 1034 can detect and process these peaks and valleys to determine speed, presence, position, direction of rotation, etc.

In another embodiment, the main body of target 1001 may be non-conductive, while feature 1014 may be conductive. In this case, eddy currents may be induced within feature 1014 but not within the main body of target 1001. Thus, the opposing magnetic field may only be present when feature 1014 is adjacent to sensor 1002 or 1004.

FIG. 10B illustrates another embodiment of system 1000 that has an irregularly shaped target 1001'. Due to the irregular shape (shown as an oval in FIG. 10B), as target 1001' rotates past sensors 1002 and 1004, some portions of the body of target 1001' may be closer to sensors 1002 and 1004, while other portions may be further away. For example, as shown, region 1016 of target 1001' is closer to sensor 1004 than region 1018 is to sensor 1002.

Because region 1016 is closer than region 1018 to magnetic field 1006, eddy current 1010 may be stronger than eddy current 1012, because the eddy currents are induced by magnetic field 1006. Accordingly, the magnetic field produced by eddy current 1010 may be stronger than the magnetic field produced by eddy current 1012. Additionally, because the magnetic field produced by eddy current 1010 is closer to sensor 1004 than the magnetic field produced by eddy current 1012 is to sensor 1002, the eddy current 1010 may have a greater effect on the magnetic flux flowing through the magnetic sensing element within sensor 1004. Thus, the magnetic field induced in region 1016 may provide a different response in the sensor than the magnetic field induced in region 1018. In other words, sensors 1002 and 1004 may detect whether the region of target 1001' adjacent to the sensor is relatively close or relatively far away from the sensor based on the extent to which the eddy current affects the magnetic field detected by the sensor. System 1000 may thus determine the position, speed, and/or direction of target 1001' based on which regions of irregularly shaped target 1001' are adjacent to the sensors as target 1001' moves.

Although shown as an elliptical target, target 1001' can have any irregular shape so long as some regions of target 1001' can be closer to the sensors while other regions can be further away. For example, target 1001' can be a toothed wheel, a toothed rack in a rack and pinion system, a square or rectangle having corners, or any other shape having protrusions or other features that can move relative to sensors 1002 and 1004.

In the case where magnetic fields 1006 and 1008 are static (i.e. DC) fields, the irregular features or shapes of targets 1001 and 1001', and/or the motion of the targets, may induce the eddy current within the target. Recall that eddy currents are caused by a changing magnetic field through a conductor. Therefore, if the target is stationary and the magnetic fields are static, no eddy currents will form because the magnetic field intersecting the target will not be changing. However, eddy currents will be created within the body of the target as it moves or rotates through a static magnetic field. If target 1001 or 1001' contains no irregular features or shapes, eddy currents having a constant strength will be induced in the body of target 1001 as it rotates. As long as the target is moving, these eddy currents can be used to detect the presence of target 1001. As the speed of target 1001 changes, the magnitude of the eddy currents, and the strength of the magnetic fields produced by the eddy currents, will also change. Thus, the sensors can also detect the speed of the target by measuring the strength of the magnetic field produced by the eddy currents.

As the features and irregular shapes of target 1001 and target 1001' move through the magnetic field, the eddy currents (and thus the magnetic fields produced by the eddy currents) will change. For example, as target 1001 rotates and feature 1014 moves through the magnetic fields, the irregular shape or conductivity of feature 1014 passing through the magnetic field causes changes to the eddy currents within target 1001. Similarly, as the irregular shape of target 1001' rotates through the magnetic fields, regions of target 1001' move relatively closer or relatively further away from the sensors. This also causes the eddy currents induced in target 1001' to change. These changes can be detected by the sensors 1002 and 1004 as presence of the target, motion of the target, speed of the target, etc.

In certain configurations, system 1000 may be able to detect direction of motion of target 1001. In one embodiment, the system is comprised of two sensors 1002, 1004, oriented as to detect different locations on the target. For example, if target 1001 is spinning in a clockwise direction, feature 1014 will pass by sensor 1002 first, and pass by sensor 1004 second. Accordingly, the signal produced by sensor 1002 to indicate the presence of feature 1014 will precede the signal produced by sensor 1004. Conversely, if target 1001 is turning in a counter-clockwise direction, the signal produced by sensor 1004 to indicate the presence of feature 1014 will precede the signal produced by sensor 1002. By monitoring the phase relationship signals produced by sensor 1002 and sensor 1004, system 1000 can determine the speed and direction of target 1001.

Although shown as a rotating target, target 1001 can also be a linear target, such as a rack in a rack and pinion system, or any other type of target that can move relative to sensors 1002 and 1004.

Figures 11, 12:
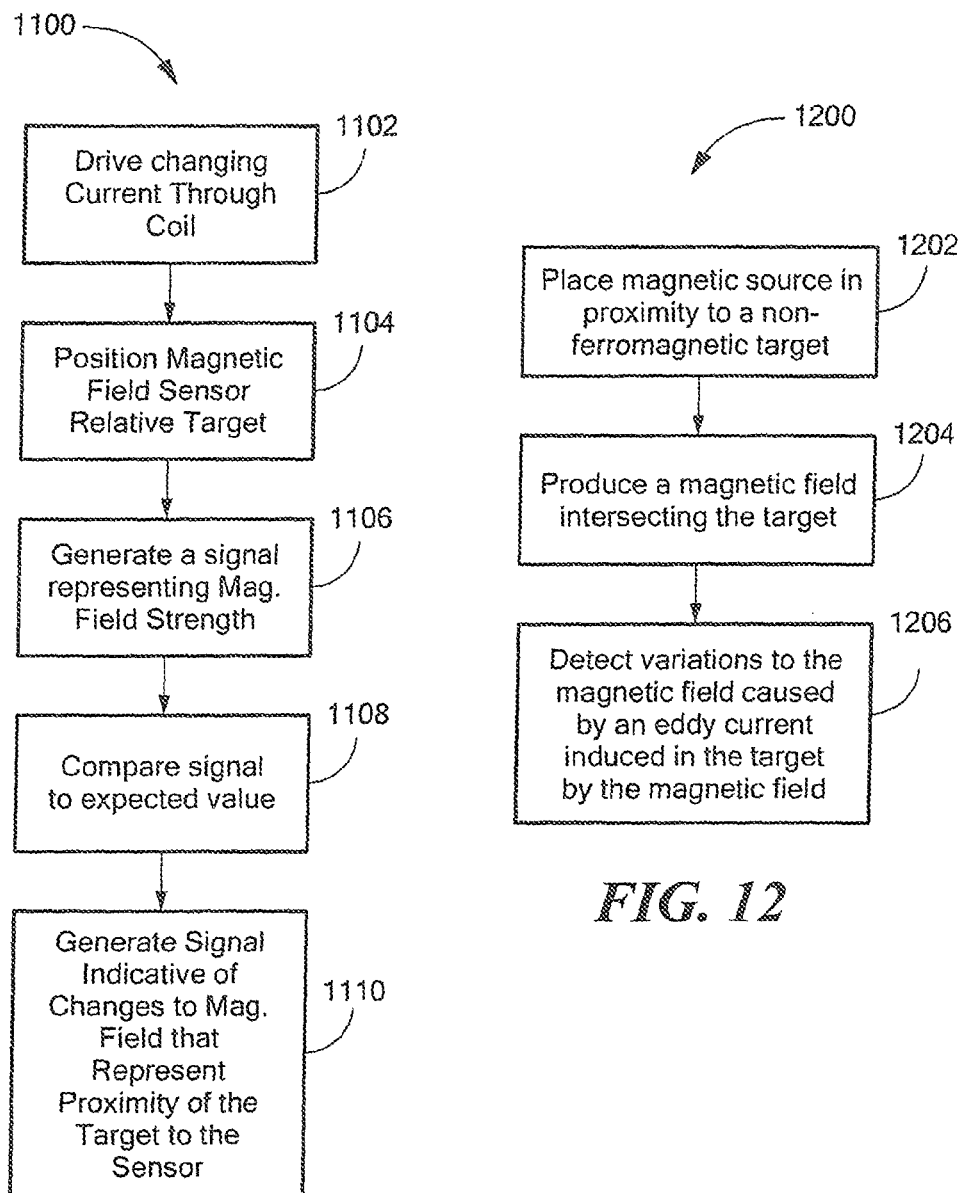
FIG. 11 is a flowchart of a method for sensing a target.
FIG. 12 is a flowchart of a method for sensing a target.

FIG. 11 is a flowchart of a process 1100 for sensing a magnetic field. In block 1102, a circuit (e.g. integrated circuit 20 in FIG. 1) may drive a changing current though a coil (e.g. coil 18). In an embodiment, the changing current may be a periodic current such as an AC current, a saw tooth pattern current, a pulsed current, a DC, or a near DC current etc. As described above, the current through the coil produces a changing magnetic field. In block 1104, a sensor (e.g. sensor 10) is positioned relative to a target. Alternatively, the target may be positioned relative to the sensor. The target may be a conductive target, a ferromagnetic target, a magnet, an electromagnet, or another type of target that generates a magnetic field. In block 1106, a signal is generated representing the strength of the combined magnetic field from the coil and magnetic field from the target. The signal may be generated by sensing element 16, for example. In block 1108, the signal is compared to an expected magnetic field strength value. In block 1110, a signal is generated that represents changes to the expected magnetic field produced by the presence of target 12. The signal may represent the proximity of the target to the sensor. The signal may be used to calculate proximity, position, speed, and direction of the target, among other properties of the target.

FIG. 12 is a flowchart of another process 1200 for sensing a magnetic field. In block 1202, a non-ferromagnetic target is placed in proximity to magnetic field source. For example, the target 1001 in FIG. 10A may be placed in proximity to sensor 1002 and/or 1004. In block 1204, a magnetic field is produced by a magnet or an electromagnet. The field intersects the target and can be sensed by sensing elements 1002 and/or 1004. In block 1206, an eddy current is induced in the target, and variations to the magnetic field caused by the eddy current are detected.

It is understood that exemplary embodiments of a magnetic sensors and systems that produce a changing magnetic field are applicable to a wide variety of applications. For example, in one embodiment, a magnetic sensor with an integrated coil is optimized for seat belt detection. In another embodiment, a magnetic sensor is optimized for seat position detection with air gaps in the order of about 0.5 to about 3 mm. In other embodiments the sensor may be optimized for air gaps as large as 1 cm. In another embodiment, a magnetic sensor is optimized to detect motion of an automotive transmission, wheel, or axle.

Having described preferred embodiments, which serve to illustrate various concepts, structures and techniques, which are the subject of this patent, it will now become apparent to those of ordinary skill in the art that other embodiments incorporating these concepts, structures and techniques may be used. It will be appreciated that the various features shown and described in connection with the various embodiments can be selectively combined. Accordingly, it is submitted that that scope of the patent should not be limited to the described embodiments but rather should be limited only by the spirit and scope of the following claims. All references cited herein are hereby incorporated herein by reference in their entirety.

What is claimed is:

1. A magnetic field sensor comprising:
    a substrate having first and second opposing surfaces;
    a magnetic source configured to provide a magnetic field to induce an eddy current in a non-ferromagnetic rotating target having a body with an oblong, oval shape affecting the eddy current, wherein the magnetic source is a coil positioned so that the substrate is between the magnetic source and the target;
    a magnetic field sensing element configured to detect the magnetic field provided by the magnetic source and a resulting magnetic field generated as a result of the eddy current and produce a signal representing a combination of the magnetic field provided by the magnetic source and the resulting magnetic field generated as a result of the eddy current; and
    a circuit formed within the substrate and coupled to receive the signal and determine a position of the rotating target,
    wherein the substrate is positioned so a plane defined by the first surface is substantially parallel to an axis of rotation of the rotating target; and
    wherein a shortest distance between the magnetic field sensing element and the rotating target changes as a result of rotation of the oblong, oval shape of the body, and a strength of the eddy current and a strength of the resulting magnetic field changes in response to changes in the shortest distance between the magnetic field sensing element and the rotating target.

2. The magnetic field sensor of claim 1 wherein the magnetic field sensing element is a giant-magnetoresistance (GMR) element.

3. The magnetic field sensor of claim 2 wherein the GMR element comprises a plurality of GMR elements in a bridge configuration.

4. The magnetic field sensor of claim 1 wherein the magnetic field sensing element is a Hall Effect element.

5. The magnetic field sensor of claim 1 wherein the coil is energized with a changing current.

6. The magnetic field sensor of claim 1 wherein the magnetic field sensing element is configured to detect a direction of rotation of the rotating target based on a direction of the eddy current.

7. The magnetic field sensor of claim 1 wherein the circuit is configured to determine proximity of the rotating target to the magnetic field sensor.

8. The magnetic field sensor of claim 7 wherein the circuit is further configured to compare the signal to an expected value.

9. The magnetic field sensor of claim 7 wherein the signal represents a closer proximity of the target in response to detection of a stronger eddy current and a further proximity in response to detection of a weaker eddy current.

10. The magnetic field sensor of claim 1 wherein the magnetic source is configured to generate a static magnetic field and the eddy current is induced by the change in the shortest distance as the target rotates.

11. The magnetic field sensor of claim 1 wherein the magnetic source is configured to generate a changing magnetic field.

12. The magnetic field sensor of claim 1 wherein the body comprises at least one feature positioned at an outer circumference of the body, the feature comprising a material that has a conductivity that differs from a conductivity of the body.

13. The magnetic field sensor of claim 12 wherein the at least one feature is non-conductive or less conductive than the body.

14. A method of detecting a magnetic field comprising:
    placing a substrate, which has a surface that supports one or more magnetic field sensing elements, on a first surface of a lead frame;
    enclosing the substrate ad a coil in a non-conductive mold material, wherein the coil is adjacent to a second surface of the lead frame opposite the first surface of the lead frame;
    placing the enclosed substrate and coil in proximity to a non-ferromagnetic rotating target so that a plane defined by the surface is substantially parallel to an axis of rotation of the non-ferromagnetic rotating target;
    producing, by the coil, a magnetic field to induce an eddy current in the non-ferromagnetic rotating target;
    causing fluctuations in the eddy current by features of the non-ferromagnetic rotating target passing through the magnetic field;
    detecting, by the one or more magnetic field sensing elements, variations in a resulting magnetic field generated by the non-ferromagnetic rotating target; and
    determining, by a processor, a position of the rotating target based on the resulting magnetic field;
    wherein a shortest distance between the one or more magnetic field sensing elements and the target changes as a result of rotation of the target, and a strength of the eddy current and a strength of the resulting magnetic field detected by the one or more magnetic field sensing elements changes in response to changes in the shortest distance between the one or more magnetic field sensing elements and the target.

15. A magnetic field sensor comprising:
    a lead frame having a first and second opposing surfaces;
    a coil adjacent to the second surface of the lead frame and configured to provide a changing magnetic field in response to being energized with a changing current to induce an eddy current in a non-ferromagnetic rotating target;

a substrate having first and second opposing surfaces, the second surface of the substrate attached to the first surface of the lead frame and the first surface of the substrate supporting:
- a magnetic field sensing element configured to detect the changing magnetic field provided by the coil and a resulting magnetic field generated as a result of the eddy current and produce a signal representing a combination of the changing magnetic field provided by the coil and the resulting magnetic field generated as a result of the eddy current; and
- a circuit formed within the substrate and coupled to receive the signal and determine a position of the rotating target;
- wherein the first surface of the substrate defines a plane that is substantially parallel to an axis of rotation of the non-ferromagnetic rotating target; and
- wherein a shortest distance between the magnetic field sensing resin element and the target changes as a result of rotation of the target, and a strength of the eddy current and a strength of the resulting magnetic field detected by the magnetic field sensing element changes in response to changes in the shortest distance between the magnetic field sensing element and the target wherein the coil is positioned so that the substrate is between the coil and the target.

16. The magnetic field sensor of claim 15 further comprising a non-conductive mold material enclosing the substrate and a portion of the lead frame, wherein the non-conductive mold material has a protrusion concentric with respect to the coil.

* * * * *

UNITED STATES PATENT AND TRADEMARK OFFICE
CERTIFICATE OF CORRECTION

PATENT NO. : 10,495,699 B2
APPLICATION NO. : 13/946417
DATED : December 3, 2019
INVENTOR(S) : Eric Burdette et al.

Page 1 of 1

It is certified that error appears in the above-identified patent and that said Letters Patent is hereby corrected as shown below:

In the Specification

Column 16, Line 25 delete "depend" and replace with --depend on--.

Column 18, Line 30 delete "phase relationship" and replace with --phase relationship of--.

In the Claims

Column 20, Line 35 delete "ad" and replace with --and--.

Column 21, Line 19 delete "sensing resin element" and replace with --sensing element--.

Signed and Sealed this
Eighth Day of September, 2020

Andrei Iancu
*Director of the United States Patent and Trademark Office*